(12) United States Patent
Bredsguard et al.

(10) Patent No.: US 9,328,305 B2
(45) Date of Patent: May 3, 2016

(54) CATALYTIC PROCESSES FOR PREPARING ESTOLIDE BASE OILS

(71) Applicant: BIOSYNTHETIC TECHNOLOGIES, LLC, Irvine, CA (US)

(72) Inventors: Jakob Bredsguard, Lake Forest, CA (US); Jeremy Forest, Honolulu, HI (US); Travis Thompson, Anaheim, CA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 0 days.

(21) Appl. No.: 14/602,752

(22) Filed: Jan. 22, 2015

(65) Prior Publication Data

US 2015/0197477 A1    Jul. 16, 2015

Related U.S. Application Data

(63) Continuation of application No. 14/095,750, filed on Dec. 3, 2013, now Pat. No. 8,975,425, which is a continuation of application No. 13/199,551, filed on Aug. 31, 2011, now Pat. No. 8,637,689.

(60) Provisional application No. 61/498,499, filed on Jun. 17, 2011, provisional application No. 61/378,891, filed on Aug. 31, 2010.

(51) Int. Cl.
  *C10M 105/34* (2006.01)
  *C07C 69/675* (2006.01)
  (Continued)

(52) U.S. Cl.
  CPC .............. *C10M 105/34* (2013.01); *C07C 57/02* (2013.01); *C07C 67/465* (2013.01); *C07C 67/48* (2013.01); *C07C 67/54* (2013.01); *C07C 69/34* (2013.01); *C07C 69/604* (2013.01); *C07C 69/675* (2013.01); *C10M 105/36* (2013.01); *C10M 107/32* (2013.01); *C10M 2207/286* (2013.01); *C10M 2207/2825* (2013.01); *C10M 2209/1023* (2013.01); *C10N 2220/022* (2013.01); *C10N 2220/023* (2013.01); *C10N 2220/027* (2013.01); *C10N 2220/028* (2013.01); *C10N 2220/10* (2013.01); *C10N 2230/02* (2013.01); *C10N 2230/64* (2013.01); *C11C 3/00* (2013.01); *C11C 3/003* (2013.01); *C11C 3/08* (2013.01)

(58) Field of Classification Search
  None
  See application file for complete search history.

(56) References Cited

U.S. PATENT DOCUMENTS

| | | |
|---|---|---|
| 2,049,072 A | 7/1936 | Mikeska et al. |
| 2,652,411 A | 9/1953 | Teeter et al. |

(Continued)

FOREIGN PATENT DOCUMENTS

| | | |
|---|---|---|
| EP | 0 352 856 | 1/1990 |
| EP | 0 665 284 | 8/1995 |

(Continued)

OTHER PUBLICATIONS

Abstract of JP 5150560.

(Continued)

*Primary Examiner* — Yate K Cutliff
(74) *Attorney, Agent, or Firm* — Jeremy Forest

(57) ABSTRACT

Provided herein are processes for preparing estolides and estolide base oils from fatty acid reactants utilizing catalysts. Further provided herein are processes for preparing carboxylic esters from at least one carboxylic acid reactant and at least one olefin.

19 Claims, 2 Drawing Sheets

(51) Int. Cl.

| | | |
|---|---|---|
| *C10M 107/32* | (2006.01) | |
| *C07C 69/34* | (2006.01) | |
| *C07C 57/02* | (2006.01) | |
| *C10M 105/36* | (2006.01) | |
| *C07C 67/465* | (2006.01) | |
| *C07C 67/48* | (2006.01) | |
| *C07C 67/54* | (2006.01) | |
| *C07C 69/604* | (2006.01) | |
| *C11C 3/00* | (2006.01) | |
| *C11C 3/08* | (2006.01) | |

(56) References Cited

U.S. PATENT DOCUMENTS

| | | | |
|---|---|---|---|
| 2,862,884 | A | 12/1958 | Dilworth et al. |
| 3,056,818 | A | 10/1962 | Werber |
| 3,184,480 | A | 5/1965 | McConnell et al. |
| 3,299,110 | A | 1/1967 | Pine |
| 3,842,019 | A | 10/1974 | Kropp |
| 4,428,850 | A | 1/1984 | Zoleski et al. |
| 4,431,673 | A | 2/1984 | Goldner et al. |
| 4,567,037 | A | 1/1986 | Ciaudelli |
| 4,639,369 | A | 1/1987 | Ciaudelli |
| 4,806,572 | A | 2/1989 | Kellett |
| 4,867,965 | A | 9/1989 | Ciaudelli |
| 5,011,629 | A | 4/1991 | Bilbo |
| 5,204,375 | A | 4/1993 | Kusakawa et al. |
| 5,380,894 | A | 1/1995 | Burg et al. |
| 5,427,704 | A | 6/1995 | Lawate |
| 5,451,332 | A | 9/1995 | Lawate |
| 5,518,728 | A | 5/1996 | Burdzy et al. |
| 5,658,863 | A | 8/1997 | Duncan et al. |
| 6,018,063 | A | 1/2000 | Isbell et al. |
| 6,160,144 | A | 12/2000 | Bongardt et al. |
| 6,316,649 | B1 | 11/2001 | Cermak et al. |
| 6,818,026 | B2 | 11/2004 | Tateno et al. |
| 6,995,108 | B1 | 2/2006 | Flessner |
| 7,119,216 | B2 | 10/2006 | Newman et al. |
| 7,252,779 | B2 | 8/2007 | Mosier et al. |
| 7,651,641 | B2 | 1/2010 | Corkran et al. |
| 7,666,828 | B2 | 2/2010 | Bernhardt et al. |
| 7,897,798 | B2 | 3/2011 | McNeff et al. |
| 7,960,599 | B2 | 6/2011 | Millis et al. |
| 8,115,021 | B2 | 2/2012 | Tupy et al. |
| 8,236,194 | B1 | 8/2012 | Bredsguard et al. |
| 8,258,326 | B1 | 9/2012 | Forest et al. |
| 8,268,199 | B1 | 9/2012 | Forest et al. |
| 8,287,754 | B1 | 10/2012 | Thompson et al. |
| 8,372,301 | B2 | 2/2013 | Bredsguard et al. |
| 8,399,389 | B2 | 3/2013 | Bredsguard et al. |
| 8,404,867 | B2 | 3/2013 | Forest et al. |
| 8,455,412 | B2 | 6/2013 | Bredsguard |
| 8,486,875 | B2 | 7/2013 | Bredsguard |
| 8,512,592 | B2 | 8/2013 | Forest et al. |
| 8,541,351 | B2 | 9/2013 | Thompson et al. |
| 8,580,985 | B2 | 11/2013 | Thompson et al. |
| 8,586,771 | B1 | 11/2013 | Lutz et al. |
| 8,633,143 | B2 | 1/2014 | Thompson et al. |
| 8,637,689 | B2 | 1/2014 | Bredsguard et al. |
| 8,829,216 | B2 | 9/2014 | Forest et al. |
| 8,859,658 | B2 | 10/2014 | Bredsguard et al. |
| 8,975,425 | B2 | 3/2015 | Thompson et al. |
| 2002/0017629 | A1 | 2/2002 | Mosier et al. |
| 2002/0193262 | A1 | 12/2002 | Kaimai et al. |
| 2004/0046146 | A1 | 3/2004 | Ankner et al. |
| 2005/0080280 | A1 | 4/2005 | Yoo |
| 2007/0092475 | A1 | 4/2007 | Wohlman et al. |
| 2007/0161832 | A1 | 7/2007 | Myllyoja et al. |
| 2008/0020956 | A1 | 1/2008 | Mosier et al. |
| 2008/0051592 | A1 | 2/2008 | McNeff et al. |
| 2009/0012324 | A1 | 1/2009 | Choi et al. |
| 2009/0159835 | A1 | 6/2009 | Kramer et al. |
| 2009/0159837 | A1 | 6/2009 | Kramer et al. |
| 2009/0187042 | A1 | 7/2009 | Ishihara et al. |
| 2010/0120643 | A1 | 5/2010 | Brown et al. |
| 2010/0145086 | A1 | 6/2010 | Schrodi et al. |
| 2010/0184855 | A1 | 7/2010 | Bernhardt et al. |
| 2010/0292328 | A1 | 11/2010 | Althaus et al. |
| 2011/0028747 | A1 | 2/2011 | Cho et al. |
| 2011/0092723 | A1 | 4/2011 | Rosas et al. |
| 2011/0105814 | A1 | 5/2011 | Kolvusalmi et al. |
| 2011/0294174 | A1 | 12/2011 | Franklin et al. |
| 2012/0018667 | A1 | 1/2012 | Krammer et al. |
| 2012/0083435 | A1 | 4/2012 | Bredsguard |
| 2012/0136168 | A1 | 5/2012 | Kersbulck et al. |
| 2012/0172269 | A1 | 7/2012 | Greaves et al. |
| 2012/0178660 | A1 | 7/2012 | Bredsguard |
| 2012/0322707 | A1 | 12/2012 | Bredsguard et al. |
| 2013/0245298 | A1 | 9/2013 | Bredsguard |
| 2013/0274493 | A1 | 10/2013 | Bredsguard |
| 2013/0324754 | A1 | 12/2013 | Bredsguard et al. |
| 2013/0338050 | A1 | 12/2013 | Bredsguard et al. |
| 2013/0340246 | A1 | 12/2013 | Thompson et al. |
| 2014/0012023 | A1 | 1/2014 | Thompson et al. |
| 2014/0039211 | A1 | 2/2014 | Lutz et al. |

FOREIGN PATENT DOCUMENTS

| | | |
|---|---|---|
| FR | 2906530 | 4/2008 |
| JP | 05150560 | 6/1993 |
| JP | 7228881 | 8/1995 |
| WO | 9925794 | 5/1999 |
| WO | 0153247 | 7/2001 |
| WO | 03011455 | 2/2003 |
| WO | 2008040864 | 4/2008 |
| WO | 2009139003 | 11/2009 |
| WO | 2011037778 | 3/2011 |
| WO | 2011106186 | 9/2011 |
| WO | 2012030398 | 3/2012 |
| WO | 2012061101 | 5/2012 |

OTHER PUBLICATIONS

Abstract of JP 7228881.
Article 19 Amendments and Letter Accompanying Replacement Sheets for counterpart application PCT/US2011/001540, filed Jan. 28, 2012.
Article 19 Amendments and Letter Accompanying Replacement Sheets for counterpart application PCT/US2012/026538, filed May 17, 2012.
Informal Comments filed in response to International Search Report and Written Opinion for counterpart application PCT/US2012/026538, filed May 17, 2012.
International Preliminary Report on Patentability for counterpart application PCT/US2011/001537, mailed Mar. 5, 2013.
International Preliminary Report on Patentability for counterpart application PCT/US2011/001540, mailed Nov. 15, 2012.
International Preliminary Report on Patentability for counterpart application PCT/US2011/050102, mailed Mar. 5, 2013.
International Search Report and Written Opinion for co-pending application PCT/US2012/039937, mailed Aug. 6, 2012.
International Search Report and Written Opinion for counterpart application PCT/US2012/026538, mailed Apr. 26, 2012.
International Search Report and Written Opinion for international application PCT/US12/68293 mailed Apr. 24, 2013.
International Search Report and Written Opinion for international application PCT/US2013/029426 mailed Jun. 6, 2013.
International Search Report and Written Opinion mailed Apr. 11, 2012 in International Application No. PCT/US2012/023933.
International Search Report and Written Opinion mailed Apr. 26, 2012 in International Application No. PCT/US2012/024260.
International Search Report and Written Opinion mailed May 15, 2012 in International Application No. PCT/US2012/026887.
International Search Report and Written Opinion mailed Nov. 23, 2011 in International Application No. PCT/US2011/001540.
International Search Report and Written Opinion mailed Nov. 23, 2011 in International Application No. PCT/US2011/050102.
International Search Report and Written Opinion mailed Nov. 30, 2011 in International Application No. PCT/US2011/001537.

(56) References Cited

OTHER PUBLICATIONS

Notice of Allowance dated Apr. 15, 2013, for U.S. Appl. No. 13/223,008, filed Aug. 31, 2011.
Notice of Allowance dated Apr. 22, 2013, for U.S. Appl. No. 13/711,388, filed Dec. 11, 2012.
Notice of Allowance dated Jan. 20, 2015, for U.S. Appl. No. 14/095,750, filed Dec. 3, 2013.
Notice of Allowance dated Jan. 4, 2013, for U.S. Appl. No. 13/199,554, filed Aug. 31, 2011.
Notice of Allowance dated Sep. 20, 2013, for U.S. Appl. No. 13/707,480, filed Dec. 6, 2012.
Office Action dated Feb. 28, 2013, for U.S. Appl. No. 13/707,480, filed Dec. 6, 2012.
Office Action dated Jan. 17, 2013, for U.S. Appl. No. 13/223,008, filed Aug. 31, 2011.
Office Action dated Jul. 3, 2012, for U.S. Appl. No. 13/199,554, filed Aug. 31, 2011.
Office Action dated Jun. 5, 2013, for U.S. Appl. No. 13/707,480, filed Dec. 6, 2012.
Office Action dated Mar. 25, 2013, for U.S. Appl. No. 13/711,388, filed Dec. 11, 2012.
Office Action dated Nov. 16, 2012, for U.S. Appl. No. 13/199,554, filed Aug. 31, 2011.
Office Action dated Nov. 2, 2012, for U.S. Appl. No. 13/199,554, filed Aug. 31, 2011.
Reply to Written Opinion for counterpart application PCT/US2011/001540, filed Jun. 28, 2012.
Written Opinion of the International Preliminary Examining Authority for Application No. PCT/US2011/050102, filed Aug. 31, 2011.
Written Opinion of the International Preliminary Examining Authority for counterpart application PCT/US2011/001540, filed Jun. 28, 2012.
Aguieiras, et al., "Estolide Synthesis Catalyzed by Immobilized Lipases", Enzyme Research, ID432746, 20011, 1-7.
Barrett, et al., "Scandium (III) or lanthanide (III) triflates as recyclable catalyst for the direct acetylation of of alcohols with acetic acid", Chem. Commun., 1997, 351-52.
Barrett, et al., "Ytterbium (III) triflates as a recyclable catalyst for the selective atom economic oxidation of benzyl alchol to benzaldehyde", Synlett, 9:, 1999, 1489-90.
Biresaw, et al., "Film-forming properties of estolides", Tribology Letters, 27(1):, 2007, 69-78.
Brutting, et al., "Produkte der Dimerisierung ungesattigter Fettsauren X: Identifizierung von Estoliden in der Anfangsphase der Dimerisierung", Fat Sci. Technol., 95(5):, 1993, 193-99.
Budarin, et al., "Versatile mesoporous carbonaceous materials for acid catalysis", Chem. Commun., 2007, 634-36.
Cann, "Polymerization of Undecylenic Acid in the Presence of Boron Fluoride", J. Am. Chem. Soc., 66(5):, 1944, 839-840.
Cermak, et al., "Comparison of a New Estolide Oxidative Stability Package", J. Am. Oil Chem. Soc., 85:, 2008, 879-885.
Cermak, et al., "Improved oxidative stability of estolide esters", Indus. Crops and Prods., 18:, 2003, 223-30.
Cermak, et al., "Synthesis and Physical Properties of Cuphea-Oleic Estolides and Esters", JAOCS, 81(3):, 2004, 297-303.
Cermak, et al., "Synthesis and physical properties of estolide-based functional fluids", Indus. Crops and Prods., 18:, 2003, 183-96.
Cermak, et al., "Synthesis and physical properties of estolides from lesquerella and castor fatty acid esters", Indus. Crops and Prods. 23:, 2006, 256-63.
Cermak, et al., "Synthesis and physical properties of mono-estolides with varying chain lengths", Indus. Crops and Prods., 29:, 2009, 205-13.
Cermak, et al., "Synthesis and Physical Properties of New Estolide Esters", Industrial Crops and Products, 46:, 2013, 386-391.
Cermak, et al., "Synthesis and Physical Properties of Tallow-Oleic Estolide 2-Ethylhexyl Esters", J. Amer. Oil Chem. Soc., 84(5):, 2007, 449-56.
Cermak, et al., "Synthesis of Estolides from Oleic and Saturated Fatty Acids", JAOCS, 78(6):, 2001, 557-65.
Choi, et al., "Iron-catalysed green synthesis of carboxylic esters by the intermolecular addition of carboxylic acids to alkenes", Chem. Commun, 2008, 777-79.
Dobbs, et al., "First Total Synthesis of the Irciniasulfonic Acids", Synlett., 4:, 2005, 652-654.
Dorwald, "Side Reactions in Organic Synthesis", Wiley: VCH, Weinheim p. IX of Preface, 2005, 1-15.
Dunn, et al., "Effect of antioxidants on the oxidative stability of methyl soyate (biodiesel)", Fuel Process. Tech., 86:, 2005, 1071-1085.
Erhan, et al., "Biodegradation of Estolides from Monounsaturated Fatty Acids", JAOCS, 74(5):, 1997, 605-07.
Erhan, et al., "Estolide Production with Modified Clay Catalysts and Process Conditions", JAOCS, 74(3):, 1997, 249-54.
Erhan, et al., "Estolides from Meadowfoam Oil Fatty Acids and Other Monounsaturated Fatty Acids", JAOCS, 70:5, May 1993, 461-465.
Garcia-Zapateiro, et al., "Viscous, thermal and tribological characterization of oleic and ricinoleic acids-derived estolides and their blends with vegetable oils", Journal of Indus. and Engin. Chem., 19:, 2013, 1289-1298.
Gast, et al., "Synthetic Lubricants from Polyhydroxystearic Acids", Indus. and Eng. Chem., 46(10):, 1954, 2205-08.
Goossen, et al., "Silver triflate-catalysed synthesis of γ-lactones from fatty acids", Green Chem., 12:, 2010, 197-200.
Harry-O'Kuru, et al., "Synthesis of Estolide Esters from cis-9-Octadecanoic Acid Estolides", JAOCS, 78(3):, 2001, 219-23.
Heydarzadeh, et al., "Esterification of Free Fatty Acids by Heterogeneous γ-Alumina-Zirconia Catalysts for Biodiesel Synthesis", World App. Sci. J., 9(11):, 2010, 1306-12.
Isbell, et al., "Acid-Catalyzed Condensation of Oleic Acid into Estolides and Polyestolides", JAOCS, 71(2):, 1994, 169-74.
Isbell, et al., "Characterization of Estolides Produced from Acid-Catalyzed Condensation of Oleic Acid", JAOCS, 71(4):, 1994, 379-83.
Isbell, et al., "Optimization of the Sulfuric Acid-Catalyzed Estolide Synthesis from Oleic Acid", JAOCS, 74(4):, 1997, 473-76.
Isbell, et al., "Physical properties of estolides and their ester derivatives", Indus. Crops and Prods., 13:, 2001, 11-20.
Isbell, et al., "Physical properties of triglyceride estolides from lesquerella and castor oils", Indus. Crops and Prods., 23, 2006, 256-253.
Ishihara, "Direct Condensation of Carboxylic Acids with Alcohols Catalyzed by Hafnium(IV) Salts", Science, 290:, 2000, 1140-42.
Jie, et al., "The use of microwave oven in transformation of long chain fatty acid esters", Lipids, 23:4, 1988, 367-369.
Karimi, "Lithium trifluoromethanesulfonate (LiOTf) as a recyclable catalyst for highly efficient acetylation of alcohols and diacetylation of aldehydes under mild and neutral reaction conditions", JOC, 68:, 2003, 4951-4954.
Komura, et al., "FeCl3•6H2O as a Versatile Catalyst for the Esterification of Steroid Alcohols with Fatty Acids", Synthesis, 21:, 2008, 3407-10.
Konishi, et al., "Effect of metal triflates on direct polycondensation of lactic acid", Polym. Bull., 64:, 2009, 435-443.
Kulkarni, et al., "Kinetics of the Catalytic Esterification of Castor Oil with Lauric Acid Using n-Butyl Benzene as a Water Entrainer", JAOCS, 80:10, 2003, 1033-1038.
Kwie, "Bismuth (III) Triflate: A Safe and Easily Handled Precursor for Triflic Acid: Application to the Esterification Reaction", Syn. Comm., 40:, 2010, 1082-1087.
Lotero, "Synthesis of Biodiesel via Acid Catalysis", Ind. Eng. Chem., 44:, 2005, 5353-5363.
Mantri, "ZrOCl2•8H2O catalysts for the esterification of long chain aliphatic carboxylic acids and alcohols. The enhancement of catalytic performance by supporting on ordered mesoporous silica", Green Chem., 7:, 2005, 677-82.
Mathers, "A General Polymerization Method Using Hydoralkoxylation and Hydrocarboxylation Reactions Catalyzed by Triflic Acid", Macromolecules, 41, 2008, 524-526.
Meier, "Plant Oil Renewable Resources as Green Alternatives in Polymer Science", Chem. Soc. Rev., 36:, 2007, 1788-1802.

(56) References Cited

OTHER PUBLICATIONS

Mol, et al., "Catalytic Metathesis of Unsaturated Fatty Acid Esters and Oils", Topics in Catalysis, 27, Nos. 1-4:, 2004, 97-104.

Nagendrappa, "Organic synthesis using clay catalysts", Resonance, 2002, 64-67.

Nakayama, et al., "Water-Tolerant and Reusable Catalysts for Direct Ester Condensation between Equimolar Amounts of Carboxylic Acids and Alcohols", Adv. Syn. Catal., 346:, 2004, 1275-79.

Nordin, et al., "New Silica Supported HClO4 as Efficient Catalysts for Estolide Synthesis from Oleic Acid", Adv. Mat. Res., 173:, 2011, 140-45.

Patil, et al., "Esterification of pthalic anhydride with n-butanol using eco-friendly solid acid catalyst sulfamic acid", Current World Environment, 5:1, 2010, 107-109.

Ross, et al., "The Polymerization of Undecylenic Acid", J. Am. Chem. Soc., 67(8):, 1945, 1275-1278.

Rudnick, L. R., "Synthetics, Mineral Oils, and Bio-Based Lubricants", CRC Press, Boca Raton, FL.; Chap. 22,, 2006, 371-74.

Sadek, E.M., "Some Study on Esterification of Maleic Acid with 2-Ethyl hexyl Alcohol", Jour. Chem. Soc. Pak., 20(4):, 1998, 271-75.

Salimon, et al., "Synthesis and Physical Properties of Estolide Ester Using Saturated Fatty Acid and Ricinoleic Acid", J. Auto. Methods and Manag. Chem., ID263624, 2011, 1-4.

Simonsick, et al., "Details structural elucidation of polyesters and acrylates using Fourier transform mass spectroscopy", Anal. Bioanal. Chem., 392:, 2008, 575-583.

Skupinska, "Oligomerization of $\alpha$-Olefins to Higher Oligomers", Chem. Rev., 91:, 1991, 613-648.

Socha, "Efficient conversion of triacylglycerols and fatty acids to biodiesel in a microwave reactor using metal triflate catalysts", Org. Biomol. Chem., 8:, 2010, 4753-56.

Suwannakarn, et al., "Stability of sulfated zirconia and the nature of the catalytically active species in the transesterification of triglycerides", J. Cat., 255:, 2008, 279-86.

Takagaki, et al., "Esterification of higher fatty acids by a novel strong solid acid", Catalysis Today, 116:, 2006, 157-61.

Taylor, et al., "Copper(II)-catalysed addition of O-H bonds to norbornene", Chem. Commun.,, 2005, 5103-05.

Teeter, et al., "Synthetic Lubricants from Hydroxystearic Acids", Indus. and Eng. Chem., 45(8):, 1953, 1777-79.

Tomoda, et al., "Characteristic Properties of Cutting Fluid Additives Derived From the Reaction Products of Hydroxyl Fatty Acids With Some Acid Anhydrides", J. of Surf. and Deter., 1:4, 1998, 533-537.

Yan, et al., "Advancements in Heterogeneous Catalysis for Biodiesel Synthesis", Top Catal., 53, 2010, 721-36.

Zerkowski, J., et al., "Estolides: From structure and function to structured and functionalized", Lipid Tech., 20(11):, 2008, 253-56.

Zhou, et al., "Solid acid catalysis of tandem isomerization-lactonization of olefinic acids", App. Cat., 333:, 2007, 238-44.

CATALYTIC PROCESSES FOR PREPARING ESTOLIDE BASE OILS

CROSS-REFERENCE TO RELATED APPLICATIONS

This application is a continuation of U.S. application Ser. No. 14/095,750, filed Dec. 3, 2013, now U.S. Pat. No. 8,975,425, which claims benefit to U.S. application Ser. No. 13/199,551, filed Aug. 31, 2011, now U.S. Pat. No. 8,637,689, which claims the benefit under 35 U.S.C. §119(e) of U.S. Provisional Patent Application No. 61/378,891, filed Aug. 31, 2010, and U.S. Provisional Patent Application No. 61/498,499, filed Jun. 17, 2011, both of which are incorporated herein by reference in their entireties for all purposes.

STATEMENT REGARDING FEDERALLY SPONSORED RESEARCH

The subject of this invention was made with support under U.S. Department of Agriculture—Agricultural Research Service Cooperative Research and Development Agreement (CRADA) Nos. 58-3K95-1-1508-M and 58-3K95-6-1147. Accordingly, the government may have certain rights in this invention.

FIELD

The present disclosure relates to catalytic processes for producing estolide compounds and compositions. The estolides described herein may be suitable for use as biodegradable base oil stocks and lubricants.

BACKGROUND

Synthetic esters such as polyol esters and adipates, low viscosity poly alpha olefins (PAO) such as PAO 2, and vegetable oils such as canola oil and oleates have been described for use industrially as biodegradable base stocks to formulate lubricants. Such base stocks may be used in the production of lubricating oils for automotives, industrial lubricants, and lubricating greases. Finished lubricants typically comprise the base oil and additives to help achieve the desired viscometric properties, low temperature behavior, oxidative stability, corrosion protection, demulsibility and water rejection, friction coefficients, lubricities, wear protection, air release, color and other properties. However, it is generally understood that biodegradability cannot be improved by using common additives that are available in today's marketplace. For environmental, economical, and regulatory reasons, it is of interest to produce biodegradable lubricating oils, other biodegradable lubricants, and compositions including lubricating oils and/or lubricants, from renewable sources of biological origin.

Estolides present a potential source of biobased, biodegradable oils that may be useful as lubricants and base stocks. Several estolide synthetic processes have been previously described, such as the homopolymerization of castor oil fatty acids or 12-hydroxystearic acid under thermal or acid catalyzed conditions, as well as the production of estolides from unsaturated fatty acids using a high temperature and pressure condensation over clay catalysts. Processes for the enzymatic production of estolides from hydroxy fatty acids present in castor oil using lipase have also been described.

In U.S. Pat. No. 6,018,063, Isbell et al. described estolide compounds derived from oleic acids under acidic conditions and having properties for use as lubricant base stocks, wherein the "capping" fatty acid comprises oleic or stearic acid. In U.S. Pat. No. 6,316,649, Cermak et al. reported estolides derived from oleic acids and having capping materials derived from $C_6$ to $C_{14}$ fatty acids.

SUMMARY

Described herein are catalytic processes for preparing estolide base oils and a carboxylic acid.

In certain embodiments, the catalytic processes include a process of producing an estolide base oil comprising: providing at least one first fatty acid reactant, at least one second fatty acid reactant, and a Lewis acid catalyst; and oligomerizing the at least one first fatty acid reactant with the at least one second fatty acid reactant in the presence of the Lewis acid catalyst to produce an estolide base oil.

In certain embodiments, the catalytic processes include a process of producing an estolide base oil comprising: providing at least one first fatty acid reactant, at least one second fatty acid reactant, and an oligomerization catalyst; and continuously oligomerizing the at least one first fatty acid reactant with the at least one second fatty acid reactant in the presence of the oligomerization catalyst to produce an estolide base oil.

In certain embodiments, the catalytic processes include a process of producing a carboxylic acid ester, comprising: providing at least one carboxylic acid reactant, at least one olefin, and a Bismuth catalyst; and reacting the at least one carboxylic acid reactant with the at least one olefin in the presence of the Bismuth catalyst to produce a carboxylic acid ester.

DETAILED DESCRIPTION

Figure 1:
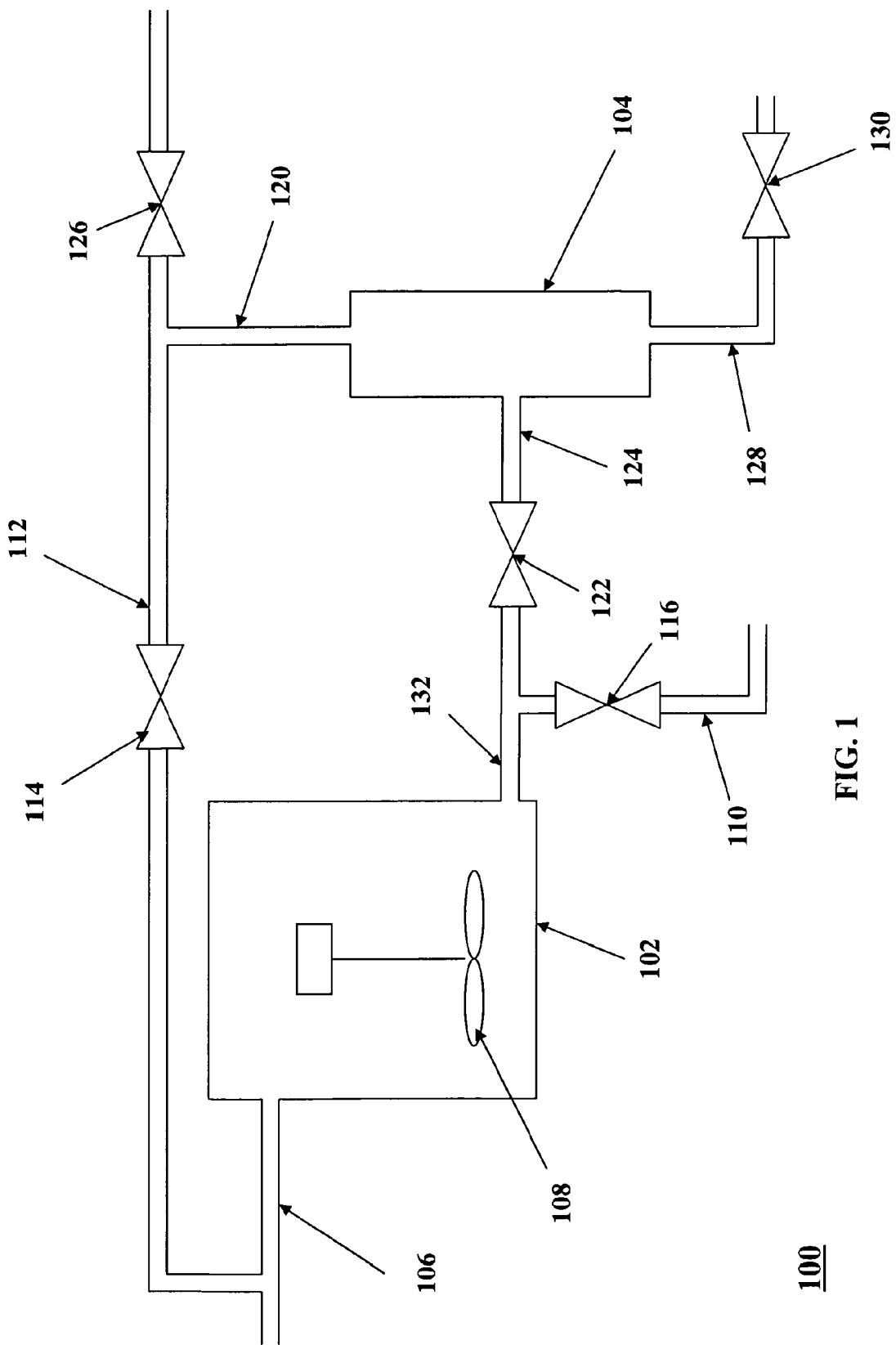
FIG. 1. schematically illustrates an exemplary process system with continuous stirred tank reactor and separation unit according to certain embodiments.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop- 1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and instead generally refer to compositions comprising one or more estolides, including mixtures of estolides. Estolide base oils and base stocks can also include compounds other than estolides.

The term "catalyst" refers to single chemical species; physical combinations of chemical species, such as mixtures, alloys, and the like; and combinations of one or more catalyst within the same region or location of a reactor or reaction vessel. Examples of catalyst include, e.g., Lewis acids, Bronsted acids, and Bismuth catalysts, wherein Lewis acids, Bronsted acids, and Bismuth catalysts may be single chemical species; physical combinations of chemical species, such as mixtures, alloys, and the like; and combinations of one or more catalyst within the same region or location of a reactor or reaction vessel.

The term "continuous" as used herein means a process wherein reactants are introduced and products withdrawn over a period of time during which the reaction continues without significant interruption. "Continuous" is not meant in any way to prohibit normal interruptions in the continuity of the process due to, for example, start-up, reactor maintenance, or scheduled shut down periods. In addition, the term "continuous" may include processes, wherein some of the reactants are charged at the beginning of the process and the remaining reactants are fed into the reactor such that the levels of reactants support continuing reaction processes. "Continuous" further includes processes where one or more reactants are intermittently added.

"Compounds" refers to compounds encompassed by structural Formula I, II, and III herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formulas I, II, and III include, but are not limited to, optical isomers of compounds of Formulas I, II, and III, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, and III covers all asymmetric variants of the compounds described herein, including isomers, racemates, enantiomers, diastereomers, and other mixtures thereof. In addition, compounds of Formula I, II, and III include Z- and E-forms (e.g., cis- and trans-forms) of compounds with double bonds. The compounds of Formula I, II, and III may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple, ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or $sp^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure. "Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Solid-supported acid" refers to an acidic compound or material that is supported by or attached to another compound or material comprising a solid or semi-solid structure. Such materials include smooth supports (e.g., metal, glass, plastic, silicon, carbon (e.g., diamond, graphite, nanotubes, fullerenes (e.g., C-60)) and ceramic surfaces) as well as textured and porous materials such as clays and clay-like materials. Such materials also include, but are not limited to, gels, rubbers, polymers, and other non-rigid materials. Solid supports need not be composed of a single material. By way of example but not by way of limitation, a solid support may comprise a surface material (e.g. a layer or coating) and a different supporting material (e.g., coated glass, coated metals and plastics, etc.) In some embodiments, solid-supported acids comprise two or more different materials, e.g., in layers. Surface layers and coatings may be of any configuration and may partially or completely cover a supporting material. It is contemplated that solid supports may comprise any combination of layers, coatings, or other configurations of multiple materials. In some embodiments, a single material provides essentially all of the surface to which other material can be attached, while in other embodiments, multiple materials of the solid support are exposed for attachment of another material. Solid supports need not be flat. Supports include any type of shape including spherical shapes (e.g., beads). Acidic moieties attached to solid support may be attached to any portion of the solid support (e.g., may be attached to an interior portion of a porous solid support material). Exemplary solid-supported acids include, but are not limited to, cation exchange resins (e.g., Amberlyst®, Dowex®); acid-activated clays (e.g., montmorillonites); polymer-supported sulfonic acids (e.g., Nafion®); and silica-support catalysts (e.g., SPA-2).

"Substituted" refers to a group in which one or more hydrogen atoms are independently replaced with the same or different substituent(s). Examples of substituents include, but are not limited to, $-R^{64}$, $-R^{60}$, $-O^-$, $-OH$, $=O$, $-OR^{60}$, $-SR^{60}$, $-S^-$, $=S$, $-NR^{60}R^{61}$, $=NR^{60}$, $-CN$, $-CF_3$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O_2)O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$, $-C(NR^{62})NR^{60}R^{61}$, $-S(O)_2NR^{60}R^{61}$, $-NR^{63}S(O)_2R^{60}$, $-NR^{63}C(O)R^{60}$, and $-S(O)R^{60}$;

wherein each $-R^{64}$ is independently a halogen; each $R^{60}$ and $R^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or $R^{60}$ and $R^{61}$ together with the nitrogen atom to which they are bonded form a heterocycloalkyl, substituted heterocycloalkyl, heteroaryl, or substituted heteroaryl ring, and $R^{62}$ and $R^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or $R^{62}$ and $R^{63}$ together with the atom to which they are bonded form one or more heterocycloalkyl, substituted heterocycloalkyl, heteroaryl, or substituted heteroaryl rings;

wherein the "substituted" substituents, as defined above for $R^{60}$, $R^{61}$, $R^{62}$, and $R^{63}$, are substituted with one or more, such as one, two, or three, groups independently selected from alkyl, -alkyl-OH, $-O$-haloalkyl, -alkyl-$NH_2$, alkoxy, cycloalkyl, cycloalkylalkyl, heterocycloalkyl, heterocycloalkylalkyl, aryl, heteroaryl, arylalkyl, heteroarylalkyl, $-O^-$, $-OH$, $=O$, $-O$-alkyl, $-O$-aryl, $-O$-heteroarylalkyl, $-O$-cycloalkyl, $-O$-heterocycloalkyl, $-SH$, $-S^-$, $=S$, $-S$-alkyl, $-S$-aryl, $-S-$ heteroarylalkyl, $-S$-cycloalkyl, $-S$-heterocycloalkyl, $-NH_2$, $=NH$, $-CN$, $-CF_3$, $-OCN$, $-SCN$, $-NO$, $-NO_2$, $=N_2$, $-N_3$, $-S(O)_2 O^-$, $-S(O)_2$, $-S(O)_2OH$, $-OS(O_2)O^-$, $-SO_2$(alkyl), $-SO_2$(phenyl), $-SO_2$(haloalkyl), $-SO_2NH_2$, $-SO_2NH$(alkyl), $-SO_2NH$(phenyl), $-P(O)(O^-)_2$, $-P(O)(O$-alkyl$)(O^-)$, $-OP(O)(O$-alkyl$)(O$-alkyl$)$, $-CO_2H$, $-C(O)O$(alkyl), $-CON$(alkyl)(alkyl), $-CONH$(alkyl), $-CONH_2$, $-C(O)$(alkyl), $-C(O)$(phenyl), $-C(O)$(haloalkyl), $-OC(O)$(alkyl), $-N$(alkyl)(alkyl), $-NH$(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acid including, for example, acetic acid, propionic acid, etc.

The term "fatty acid reactant" refers to any compound or composition comprising a fatty acid residue that is capable of undergoing oligomerization with another fatty acid or fatty acid reactant. For example, in certain embodiments, the fatty acid reactant may comprise a saturated or unsaturated fatty acid or fatty acid oligomer. In certain embodiments, a fatty acid oligomer may comprise a first fatty acid that has previously undergone oligomerization with one or more second fatty acids to form an estolide, such as an estolide having a low EN (e.g., dimer). It is understood that a "first" fatty acid reactant can comprise the same structure as a "second" fatty acid reactant. For example, in certain embodiments, a reaction mixture may only comprise oleic acid, wherein the first fatty acid reactant and second fatty acid reactant are both oleic acid.

The term "acid-activated clay" refers to clays that are derived from the naturally occurring ore bentonite or the mineral montmorillonite and includes materials prepared by calcination, washing or leaching with mineral acid, ion exchange or any combination thereof, including materials which are often called montmorillonites, acid-activated montmorillonites and activated montmorillonites. In certain embodiments, these clays may contain Bronsted as well as Lewis acid active sites with many of the acidic sites located within the clay lattice. Such clays include, but are not limited to the materials denoted as montmorillonite K10, montmorillonite clay, clayzic, clayfen, the Engelhardt series of catalysts related to and including X-9107, X9105, Girdler KSF, Tonsil and K-catalysts derived from montmorillonite, including but not limited to K5, K10, K20 and K30, KSF, KSF/O, and KP10. Other acid-activated clays may include X-9105 and X-9107 acid washed clay catalysts marketed by Engelhard.

The term "zeolite" refers to mesoporous aluminosilicates of the group IA or group HA elements and are related to montmorillonite clays that are or have been acid activated. Zeolites may comprise what is considered an "infinitely" extending framework of AlO4 and SiO4 tetrahedra linked to each other by the sharing of oxygens. The framework structure may contain channels or interconnecting voids that are occupied by cations and water molecules. Acidic character may be imparted or enhanced by ion exchange of the cations, such as with ammonium ions and subsequent thermal deamination or calcination. The acidic sites may primarily be located within the lattice pores and channels. In certain instances, zeolites include, but are not limited to, the beta-type zeolites as typified by CP814E manufactured by Zeolyst International, the mordenite form of zeolites as typified by CBV21A manufactured by Zeolyst International, the Y-type zeolites as typified by CBV-720 manufactured by Zeolyst International, and the ZSM family of zeolites as typified by ZSM-5, and ZSM-11.

All numerical ranges herein include all numerical values and ranges of all numerical values within the recited range of numerical values.

The present disclosure relates to estolide compounds, compositions and methods of making the same. In certain embodiments, the estolide compounds and compositions are useful as estolide base oil or estolide base oil feedstock. In certain embodiments, the present disclosure relates to processes for preparing estolides that utilize catalysts that can be recovered and reused. In certain embodiments, the present disclosure relates to efficient continuous and semi-continuous flow processes for preparing estolide base oils, base stocks, and lubricants. In certain embodiments, the present disclosure relates to catalysts that can be recovered and reused and/or used in efficient continuous and semi-continuous flow processes. In certain embodiments, the catalysts and methods disclosed herein may be useful in preparing an estolide compound of Formula I:

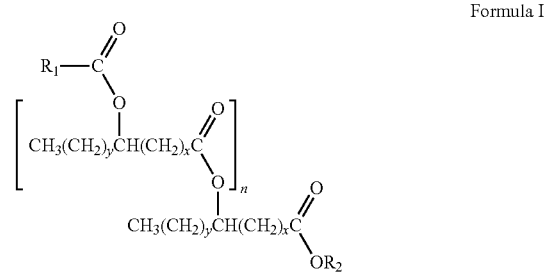

Formula I wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is an integer selected from 1 to 12;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

In certain embodiments, the catalysts and methods disclosed herein may be useful in preparing an estolide compound of Formula II

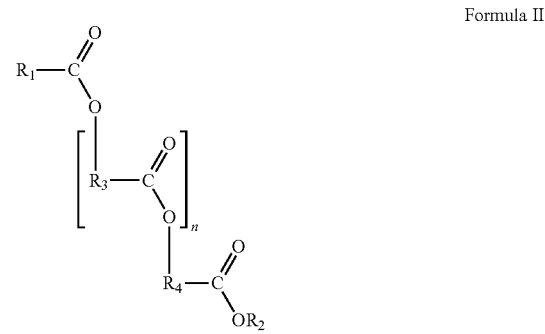

Formula II wherein n is an integer greater than or equal to 1;

$R_2$ is selected from hydrogen and optionally substituted alkyl that is saturated or unsaturated, and branched or unbranched; and $R_1$, $R_3$, and $R_4$, independently for each occurrence, are selected from optionally substituted alkyl that is saturated or unsaturated, and branched or unbranched.

In certain embodiments, the catalysts and methods disclosed herein may be useful in preparing an estolide compound of Formula III:

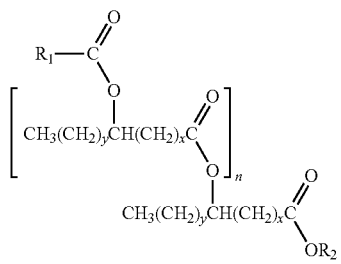

Formula III wherein x is, independently for each occurrence, an integer selected from 0, 1, 2, 3, 4, 5, 6, 7, 8, 9, 10, 11, 12, 13, 14, 15, 16, 17, 18, 19, and 20;

y is, independently for each occurrence, an integer selected from 0, 1, 2, 3, 4, 5, 6, 7, 8, 9, 10, 11, 12, 13, 14, 15, 16, 17, 18, 19, and 20;

n is equal to or greater than 0;

$R_1$ is an optionally substituted alkyl that is saturated or unsaturated, and branched or unbranched; and $R_2$ is selected from hydrogen and optionally substituted alkyl that is saturated or unsaturated, and branched or unbranched;

wherein each fatty acid chain residue of said at least one compound is independently optionally substituted.

The term "chain", or "fatty acid chain," or "fatty acid chain residue," as used with respect to the estolide compounds of Formula I, II, and III refer to one or more of the fatty acid residues incorporated in estolide compounds, e.g., $R_3$ or $R_4$ of Formula II, or the structures represented by $CH_3(CH_2)_y CH(CH_2)_x C(O)O-$ in Formula I or III.

The $R_1$ in Formula I, II, and III at the top of each Formula shown is an example of what may be referred to as a "cap" or "capping material," as it "caps" the top of the estolide. Similarly, the capping group may be an organic acid residue of general formula —OC(O)-alkyl, i.e., a carboxylic acid with a substituted or unsubstituted, saturated or unsaturated, and/or branched or unbranched alkyl as defined herein, or a formic acid residue. In certain embodiments, the "cap" or "capping group" is a fatty acid. In certain embodiments, the capping group, regardless of size, is substituted or unsubstituted, saturated or unsaturated, and/or branched or unbranched. The cap or capping material may also be referred to as the primary or alpha (α) chain.

Depending on the manner in which the estolide is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments, it may be desirable to provide a method of providing a saturated capped estolide by hydrogenating an unsaturated cap using any suitable methods available to those of ordinary skill in the art. Hydrogenation may be used with various sources of the fatty-acid feedstock, which may include mono- and/or poly-unsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The $R_4 C(O)O-$ of Formula II or the $CH_3(CH_2)_y CH(CH_2)-C(O)O-$ of Formula I and III serve as the "base" or "base chain residue" of the estolide. Depending on the manner in which the estolide is synthesized, the base organic acid or fatty acid residue may be the only residue that remains in its free-acid form after the initial synthesis of the estolide. However, in an effort to alter or improve the properties of the estolide, in certain embodiments, the free acid may be reacted with any number of substituents. For example, in certain embodiments, it may be desirable to react the free acid estolide with alcohols, glycols, amines, or other suitable reactants to provide the corresponding ester, amide, or other reaction products. The base or base chain residue may also be referred to as tertiary or gamma (γ) chains.

The $R_3 C(O)O-$ of Formula II or structure $CH_3(CH_2)_y CH(CH_2)_x C(O)O-$ of Formula I and III are linking residues that link the capping material and the base fatty-acid residue together. There may be any number of linking residues in the estolide, including when n=0 and the estolide is in its dimer form. Depending on the manner in which the estolide is prepared, in certain embodiments, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta (β) chains.

In certain embodiments, the cap is an acetyl group, the linking residue(s) is one or more fatty acid residues, and the base chain residue is a fatty acid residue. In certain embodiments, the linking residues present in an estolide differ from one another. In certain embodiments, one or more of the linking residues differs from the base chain residue.

In some embodiments, the estolide comprises fatty-acid chains of varying lengths. In some embodiments with estolides according to Formula I and III, x is, independently for each occurrence, an integer selected from 0 to 20, 0 to 18, 0 to 16, 0 to 14, 1 to 12, 1 to 10, 2 to 8, 6 to 8, or 4 to 6. In some embodiments with estolides according to Formula I and III, x is, independently for each occurrence, an integer selected from 7 and 8. In some embodiments with estolides according to Formula I, x is, independently for each occurrence, an integer selected from 0, 1, 2, 3, 4, 5, 6, 7, 8, 9, 10, 11, 12, 13, 14, 15, 16, 17, 18, 19, or 20.

In some embodiments with estolides according to Formula I and III, y is, independently for each occurrence, an integer selected from 0 to 20, 0 to 18, 0 to 16, 0 to 14, 1 to 12, 1 to 10, 2 to 8, 6 to 8, or 4 to 6. In some embodiments with estolides according to Formula I and III, y is, independently for each occurrence, an integer selected from 7 and 8. In some embodiments with estolides according to Formula I, y is, independently for each occurrence, an integer selected from 0, 1, 2, 3, 4, 5, 6, 7, 8, 9, 10, 11, 12, 13, 14, 15, 16, 17, 18, 19, or 20. In some embodiments with estolides according to Formula I, x+y is, independently for each chain, an integer selected from 0 to 40, 0 to 20, 10 to 20, or 12 to 18. In some embodiments with estolides according to Formula I and III, x+y is, independently for each chain, an integer selected from 13 to 15. In some embodiments with estolides according to Formula I and III, x+y is 15. In some embodiments with estolides according to Formula I, x+y is, independently for each chain, an integer selected from 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40.

In some embodiments, the estolide of Formula I, II, or III may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I, II, and III comprises the trimer. In some embodiments, n is an integer selected from 0, 1, 2, 3, 4, 5, 6, 7, 8, 9, 10, 11, 12, 13, 14, 15, 16, 17, 18, 19, or 20.

In some embodiments, $R_1$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_1$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_1$ is selected from $C_{13}$ to $C_{17}$ alkyl, such as from $C_{13}$ alkyl, $C_{15}$ alkyl, and $C_{17}$ alkyl. In some embodiments, $R_1$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_2$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl. As noted above, in certain embodiments, one or more of the estolides' properties is manipulated by altering the length of $R_1$ and/or its degree of saturation. In certain embodiments, the level of substitution on $R_1$ may also be altered to change or even improve the estolides' properties. Without being bound to any particular theory, in certain embodiments, including polar substituents on $R_1$, such as one or more hydroxy groups, may increase the viscosity of the estolide, while increasing pour point. Accordingly, in some embodiments, $R_1$ will be unsubstituted or optionally substituted with a group that is not hydroxyl.

In some embodiments, the estolide is in its free-acid form, wherein $R_2$ of Formulas I, II, and III is hydrogen. In some embodiments, $R_2$ is selected from optionally substituted alkyl that is saturated or unsaturated, and branched or unbranched. In some embodiments, the $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, in some embodiments, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl. Such groups at the $R_2$ position may be derived from esterification of the free-acid estolide using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ may be sourced from certain alcohols to provide branched alkyls such as isostearyl and isopalmityl. It should be understood that such isopalmityl and isostearyl akyl groups may cover any branched variation of $C_{16}$ and $C_{18}$, respectively. For example, the estolides described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in certain embodiments, large, highly-branched alkyl groups (e.g., isopalmityl and isostearyl) at the $R_2$ position of the estolides can provide at least one way to increase the lubricant's viscosity, while substantially retaining or even reducing its pour point.

In some embodiments, the compounds described herein may comprise a mixture of two or more estolide compounds of Formula I, II, or III. It is possible to characterize the chemical makeup of an estolide, a mixture of estolides, or a composition comprising estolides, by using the compound's, mixture's, or composition's measured estolide number (EN). The EN represents the average number of fatty acids added to the base fatty acid. The EN also represents the average number of estolide linkages per molecule:

$$EN=n+1$$

wherein n is the number of secondary (β) fatty acids. Accordingly, a single estolide compound will have an EN that is a whole number, for example for dimers, trimers, and tetramers:

dimer EN=1
trimer EN=2
tetramer EN=3

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions described herein may comprise a mixture of two or more estolides having an EN that is an integer or fraction of an integer that is greater than 4.5, or even 5.0. In some embodiments, the EN may be an integer or fraction of an integer selected from about 1.0 to about 5.0. In some embodiments, the EN is an integer or fraction of an integer selected from 1.2 to about 4.5. In some embodiments, the EN is selected from a value greater than 1.0, 1.2, 1.4, 1.6, 1.8, 2.0, 2.2, 2.4, 2.6, 2.8, 3.0, 3.4, 3.6, 3.8, 4.0, 4.2, 4.4, 4.6, 4.8, 5.0, 5.2, 5.4, 5.6, and 5.8. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. In some embodiments the estolides described herein may comprise at least one compound of Formula II:

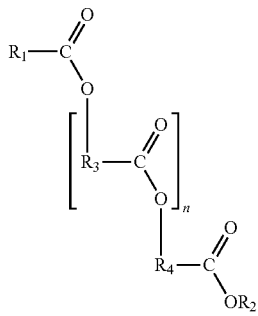

Formula II wherein n is greater than or equal to 1;

$R_2$ is selected from hydrogen and optionally substituted alkyl that is saturated or unsaturated, and branched or unbranched; and $R_1$, $R_3$ and $R_4$, independently for each occurrence, are selected from optionally substituted alkyl that is saturated or unsaturated, and branched or unbranched.

In some embodiments, n is an integer selected from 1 to 20. In some embodiments, n is an integer selected from 1 to 12. In some embodiments, n is an integer selected from 1, 2, 3, 4, 5, 6, 7, 8, 9, 10, 11, 12, 13, 14, 15, 16, 17, 18, 19 and 20. In some embodiments, one or more R3 differs from one or more other R3 in a compound of Formula II. In some embodiments, one or more R3 differs from R4 in a compound of Formula II. In some embodiments, if the compounds of Formula II are prepared from one or more polyunsaturated fatty acids, it is possible that one or more of R1, R3 and R4 will have one or more sites of unsaturation. In some embodiments, if the compounds of Formula II are prepared from one or more branched fatty acids, it is possible than one or more of R1, R3, and R4 will be branched.

In some embodiments, R3 and R4 can be CH3(CH2)yCH(CH2)x-, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both R3 and R4 are CH3(CH2)yCH(CH2)x-, the compounds may be compounds according to Formula I and III.

Without being bound to any particular theory, in certain embodiments, altering the EN to produce estolides having desired viscometric properties while substantially retaining or even reducing pour point. For example, in some embodiments, exhibit a decreased pour point upon increasing the EN value. Accordingly, in certain embodiments, a method is provided for retaining or decreasing the pour point of an estolide base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil is accomplished by distillation, chromatography, membrane separation, phase separation, affinity separation, solvent extraction, or combinations thereof. In some embodiments, the distillation takes place at a temperature and/or pressure that is suitable to separate the estolide base oil into different "cuts" that individually exhibit different EN values. In some embodiments, this may be accomplished by subjecting the base oil temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

In some embodiments, estolide compounds and compositions exhibit an EN that is greater than or equal to 1, such as an integer or fraction of an integer selected from about 1.0 to about 2.0. In some embodiments, the EN is an integer or fraction of an integer selected from about 1.0 to about 1.6. In some embodiments, the EN is a fraction of an integer selected from about 1.1 to about 1.5. In some embodiments, the EN is selected from a value greater than 1.0, 1.1, 1.2, 1.3, 1.4, 1.5, 1.6, 1.7, 1.8, and 1.9. In some embodiments, the EN is selected from a value less than 1.1, 1.2, 1.3, 1.4, 1.5, 1.6, 1.7, 1.8, 1.9, and 2.0.

In some embodiments, the EN is greater than or equal to 1.5, such as an integer or fraction of an integer selected from about 1.8 to about 2.8. In some embodiments, the EN is an integer or fraction of an integer selected from about 2.0 to about 2.6. In some embodiments, the EN is a fraction of an integer selected from about 2.1 to about 2.5. In some embodiments, the EN is selected from a value greater than 1.8, 1.9, 2.0, 2.1, 2.2, 2.3, 2.4, 2.5, 2.6, and 2.7. In some embodiments, the EN is selected from a value less than 1.9, 2.0, 2.1, 2.2, 2.3, 2.4, 2.5, 2.6, 2.7, and 2.8. In some embodiments, the EN is about 1.8, 2.0, 2.2, 2.4, 2.6, or 2.8.

In some embodiments, the EN is greater than or equal to about 3, such as an integer or fraction of an integer selected from about 3.0 to about 4.0. In some embodiments, the EN is a fraction of an integer selected from about 3.2 to about 3.8. In some embodiments, the EN is a fraction of an integer selected from about 3.3 to about 3.7. In some embodiments, the EN is selected from a value greater than 3.0, 3.1, 3.2, 3.3, 3.4, 3.5, 3.6, 3.7, 3.8, and 3.9. In some embodiments, the EN is selected from a value less than 3.1, 3.2, 3.3, 3.4, 3.5, 3.6, 3.7, 3.8, 3.9, and 4.0. In some embodiments, the EN is about 3.0, 3.2, 3.4, 3.6, 3.8, or 4.0. In some embodiments, the EN is greater than or equal to about 4, such as an integer or fraction of an integer selected from about 4.0 to about 5.0. In some embodiments, the EN is a fraction of an integer selected from about 4.2 to about 4.8. In some embodiments, the EN is a fraction of an integer selected from about 4.3 to about 4.7. In some embodiments, the EN is selected from a value greater than 4.0, 4.1, 4.2, 4.3, 4.4, 4.5, 4.6, 4.7, 4.8, and 4.9. In some embodiments, the EN is selected from a value less than 4.1, 4.2, 4.3, 4.4, 4.5, 4.6, 4.7, 4.8, 4.9, and 5.0. In some embodiments, the EN is about 4.0, 4.2, 4.4, 4.6, 4.8, or 5.0.

In some embodiments, the EN is greater than or equal to about 5, such as an integer or fraction of an integer selected from about 5.0 to about 6.0. In some embodiments, the EN is a fraction of an integer selected from about 5.2 to about 5.8. In some embodiments, the EN is a fraction of an integer selected from about 5.3 to about 5.7. In some embodiments, the EN is selected from a value greater than 5.0, 5.1, 5.2, 5.3, 5.4, 5.5, 5.6, 5.7, 5.8, and 5.9. In some embodiments, the EN is selected from a value less than 5.1, 5.2, 5.3, 5.4, 5.5, 5.6, 5.7, 5.8, 5.9, and 6.0. In some embodiments, the EN is selected from a value less than 5.1, 5.2, 5.3, 5.4, 5.5, 5.6, 5.7, 5.8, 5.9, and 6.0. In some embodiments, the EN is about 5.0, 5.2; 5.4, 5.4, 5.6, 5.8, or 6.0.

Typically, estolide base oil exhibit certain lubricity, viscosity, and/or pour point characteristics. For example, suitable viscosity characteristics of the base oil may range from about 10 cSt to about 250 cSt at 40° C., and/or about 3 cSt to about 30 cSt at 100° C. In some embodiments, the estolide base oil may exhibit viscosities within a range from about 50 cSt to about 150 cSt at 40° C., and/or about 10 cSt to about 20 cSt at 100° C.

In some embodiments, the estolide base oil may exhibit viscosities less than about 55 cSt at 40° C. or less than about 45 cSt at 40° C., and/or less than about 12 cSt at 100° C. or less than about 10 cSt at 100° C. In some embodiments, the estolide base oil may exhibit viscosities within a range from about 25 cSt to about 55 cSt at 40° C., and/or about 5 cSt to about 11 cSt at 100° C. In some embodiments, the estolide base oil may exhibit viscosities within a range from about 35 cSt to about 45 cSt at 40° C., and/or about 6 cSt to about 10 cSt at 100° C. In some embodiments, the estolide base oil may exhibit viscosities within a range from about 38 cSt to about 43 cSt at 40° C., and/or about 7 cSt to about 9 cSt at 100° C.

In some embodiments, the estolide base oil may exhibit viscosities less than about 120 cSt at 40° C. or less than about 100 cSt at 40° C., and/or less than about 18 cSt at 100° C. or less than about 17 cSt at 100° C. In some embodiments, the estolide base oil may exhibit a viscosity within a range from about 70 cSt to about 120 cSt at 40° C., and/or about 12 cSt to about 18 cSt at 100° C. In some embodiments, the estolide base oil may exhibit viscosities within a range from about 80 cSt to about 100 cSt at 40° C., and/or about 13 cSt to about 17 cSt at 100° C. In some embodiments, the estolide base oil may exhibit viscosities within a range from about 85 cSt to about 95 cSt at 40° C., and/or about 14 cSt to about 16 cSt at 100° C.

In some embodiments, the estolide base oil may exhibit viscosities greater than about 180 cSt at 40° C. or greater than about 200 cSt at 40° C., and/or greater than about 20 cSt at 100° C. or greater than about 25 cSt at 100° C. In some embodiments, the estolide base oil may exhibit a viscosity within a range from about 180 cSt to about 230 cSt at 40° C., and/or about 25 cSt to about 31 cSt at 100° C. In some embodiments, estolide base oil may exhibit viscosities within a range from about 200 cSt to about 250 cSt at 40° C., and/or about 25 cSt to about 35 cSt at 100° C. In some embodiments, estolide base oil may exhibit viscosities within a range from about 210 cSt to about 230 cSt at 40° C., and/or about 28 cSt to about 33 cSt at 100° C. In some embodiments, the estolide base oil may exhibit viscosities within a range from about 200 cSt to about 220 cSt at 40° C., and/or about 26 cSt to about 30 cSt at 100° C. In some embodiments, the estolide base oil may exhibit viscosities within a range from about 205 cSt to about 215 cSt at 40° C., and/or about 27 cSt to about 29 cSt at 100° C.

In some embodiments, the estolide base oil may exhibit viscosities less than about 45 cSt at 40° C. or less than about 38 cSt at 40° C., and/or less than about 10 cSt at 100° C. or less than about 9 cSt at 100° C. In some embodiments, the estolide base oil may exhibit a viscosity within a range from about 20 cSt to about 45 cSt at 40° C., and/or about 4 cSt to about 10 cSt at 100° C. In some embodiments, the estolide base oil may exhibit viscosities within a range from about 28 cSt to about 38 cSt at 40° C., and/or about 5 cSt to about 9 cSt at 100° C. In some embodiments, the estolide base oil may exhibit viscosities within a range from about 30 cSt to about 35 cSt at 40° C., and/or about 6 cSt to about 8 cSt at 100° C.

In some embodiments, the estolide base oil may exhibit viscosities less than about 80 cSt at 40° C. or less than about 70 cSt at 40° C., and/or less than about 14 cSt at 100° C. or less than about 13 cSt at 100° C. In some embodiments, the estolide base oil may exhibit a viscosity within a range from about 50 cSt to about 80 cSt at 40° C., and/or about 8 cSt to about 14 cSt at 100° C. In some embodiments, the estolide base oil may exhibit viscosities within a range from about 60 cSt to about 70 cSt at 40° C., and/or about 9 cSt to about 13 cSt at 100° C. In some embodiments, the estolide base oil may exhibit viscosities within a range from about 63 cSt to about 68 cSt at 40° C., and/or about 10 cSt to about 12 cSt at 100° C.

In some embodiments, the estolide base oil may exhibit viscosities greater than about 120 cSt at 40° C. or greater than about 130 cSt at 40° C., and/or greater than about 15 cSt at 100° C. or greater than about 18 cSt at 100° C. In some embodiments, the estolide base oil may exhibit a viscosity within a range from about 120 cSt to about 150 cSt at 40° C., and/or about 16 cSt to about 24 cSt at 100° C. In some embodiments, the estolide base oil may exhibit viscosities within a range from about 130 cSt to about 160 cSt at 40° C., and/or about 17 cSt to about 28 cSt at 100° C. In some embodiments, the estolide base oil may exhibit viscosities within a range from about 130 cSt to about 145 cSt at 40° C., and/or about 17 cSt to about 23 cSt at 100° C. In some embodiments, the estolide base oil may exhibit viscosities within a range from about 135 cSt to about 140 cSt at 40° C., and/or about 19 cSt to about 21 cSt at 100° C.

The estolides may exhibit desirable low-temperature pour point properties. In some embodiments, the estolide base oil may exhibit a pour point lower than about −25° C., about −35° C., −40° C., or even about −50° C. In some embodiments, the estolides have a pour point of about −25° C. to about −45° C. In some embodiments, the pour point falls within a range of about −30° C. to about −40° C., about −34° C. to about −38° C., about −30° C. to about −45° C., −35° C. to about −45° C., 34° C. to about −42° C., about −38° C. to about −42° C., or about 36° C. to about −40° C. In some embodiments, the pour point falls within the range of about −27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C. about −37° C., about −38° C., about −39° C., about −40° C., about −41° C., about −42° C., about −43° C., about −44° C., and about −45° C. In some embodiments, the lower bound of the pour point is greater than about −55° C., about −54° C., about −53° C., about −52° C., −51, about −50° C., about −49° C., about −48° C., about −47° C., about −46° C., or about −45° C.

In addition, in certain embodiments, estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher N. Thus, in certain embodiments, it may be desirable to reduce the N of the estolides in an effort to increase the oil's oxidative stability, while also decreasing harmful deposits and the corrosiveness of the oil.

In some embodiments, estolide compounds and compositions have an IV of less than about 40 cg/g or less than about 35 cg/g. In some embodiments, estolides have an N of less than about 30 cg/g, less than about 25 cg/g, less than about 20 cg/g, less than about 15 cg/g, less than about 10 cg/g, or less than about 5 cg/g. The N of a composition may be reduced by decreasing the estolide's degree of unsaturation. In certain embodiments, this may be accomplished by, for example, by increasing the amount of saturated capping materials relative to unsaturated capping materials when synthesizing the estolides. Alternatively, in certain embodiments, IV may be reduced by hydrogenating estolides having unsaturated caps. In certain embodiments, a process for preparing an estolide base oil comprising providing at least one first fatty acid reactant and at least one second fatty acid reactant and a Lewis acid can be conducted with feedstock comprising myristoleic, palmitoleic, oleic acids, or combinations thereof.

In some embodiments, the process for preparing an estolide base oil is a batch, semi-continuous, or continuous process, wherein the Lewis acid catalyst is $Bi(OTf)_3$, and at least a portion of the oligomerizing step takes place in the presence of applied microwave radiation, at a pressure of between 5 and 15 torr abs, and at a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, and at least a portion of the oligomerizing step takes place at a pressure of between 5 and 15 torr abs, and a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, and at least a portion of the oligomerizing step takes place at a pressure of less than 5 torr or greater than 15 torr abs, and a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, and at least a portion of the oligomerizing step takes place in the presence of applied microwave radiation, at a pressure of between 5 and 15 torr abs, and at a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, and at least a portion of the oligomerizing step takes place at a pressure of between 5 and 15 torr abs, and a temperature of about 50° C. to about 60° C. about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C., about 65° C. to about 75° C., or about 70° C. to about 80° C.

In some embodiments, the process for preparing an estolide base oil is a batch, semi-continuous, or continuous process, wherein the Lewis acid catalyst is $Bi(OTf)_3$, and at least a portion of the oligomerizing step takes place at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, and at least a portion of the oligomerizing step takes place in the presence of applied microwave radiation, at a pressure of between 5 and 15 torr abs, and at a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, and at least a portion of the oligomerizing step takes place at a pressure of between 5 and 15 torr abs, and a temperature of about 50° C. to about 60° C., about 55° C. to about 65° C. about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, at least a portion of the oligomerizing step takes place in the presence of applied microwave radiation, at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, and at least a portion of the oligomerizing step takes place at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, and at least a portion of the oligomerizing step takes place in the presence of applied microwave radiation, at a pressure of between 5 and 15 torr abs, and at a temperature of about 50° C. to about 60° C., about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, at a pressure of between 5 and 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Cu(OTf)_2$, at a pressure of less than 5 torr or greater than 15 torr abs, and a temperature of about 50° C. to about 60° C., about 55° C. to about 65° C. about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, and at least a portion of the oligomerizing step takes place in the presence of applied microwave radiation, at a pressure of between 5 and 15 torr abs, and at a temperature of about 50° C. to about 60° C., about 55° C. to about 65° C., about 60° C. to about 70° C. about 65° C. to about 75° C., and about 70° C. to about 80° C.

In some embodiments, the process for preparing an estolide base oil is a batch, semi-continuous, or continuous process, wherein the Lewis acid catalyst is $Fe(OTf)_3$, at a pressure of between 5 and 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, and at least a portion of the oligomerizing step takes place in the presence of applied microwave radiation, at a pressure of between 5 and 15 torr abs, and at a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, and at least a portion of the oligomerizing step takes place at a pressure of between 5 and 15 torr abs, and a temperature of about 50° C. to about 60° C. about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the process for preparing an estolide base oil is a batch, semi-continuous, or continuous process, wherein the Lewis acid catalyst is $Fe(OTf)_3$, at least no portion of the oligomerizing step takes place in the presence of applied microwave radiation, at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C.

The present disclosure also provides an improved process for esterification to provide esters. In some embodiments, the process is a batch, semi-continuous, or continuous process.

In some embodiments, the esterifying is catalyzed by $Bi(OTf)_3$, or a combinations thereof, and at least a portion of the oligomerizing step takes place in the presence of applied microwave radiation, at a pressure of between 5 and 15 torr abs, and at a temperature of about 50° C. to about 60° C., about 55° C. to about 65° C., about 60° C. to about 70° C. about 65° C. to about 75° C., or about 70° C. to about 80° C.

In some embodiments, the esterifying is catalyzed by $Bi(OTf)_3$, or a combinations thereof, and at least a portion of the oligomerizing step takes place at a pressure of between 5 and 15 torr abs, and a temperature of about 50° C. to about 60° C. about 55° C. to about 65° C., about 60° C. to about 70° C. about 65° C. to about 75° C., or about 70° C. to about 80° C.

In some embodiments, the esterifying is catalyzed by Bi(OTf)$_3$, or a combinations thereof, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the esterifying is catalyzed by Bi(OTf)$_3$, or a combinations thereof, and at least a portion of the oligomerizing step takes place at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C.

In some embodiments, the esterifying is catalyzed by Bi(OTf)$_3$, or a combinations thereof, and at least a portion of the oligomerizing step takes place in the presence of applied microwave radiation, at a pressure of between 5 and 15 torr abs, and at a temperature of about 50° C. to about 60° C. about 55° C. to about 65° C. about 60° C. to about 70° C. about 65° C. to about 75° C., or about 70° C. to about 80° C.

In some embodiments, the esterifying is catalyzed by Bi(OTf)$_3$, or a combinations thereof at a pressure of between 5 and 15 torr abs, and a temperature of about 50° C. to about 60° C., about 55° C. to about 65° C., about 60° C. to about 70° C. about 65° C. to about 75° C., or about 70° C. to about 80° C.

In some embodiments, the esterifying is catalyzed by Bi(OTf)$_3$, or a combinations thereof, at least a portion of the oligomerizing step takes place in the presence of applied microwave radiation, at a pressure of less than 5 torr or greater than 15 torr abs, and a temperature of about 50° C. to about 60° C., about 55° C. to about 65° C., about 60° C. to about 70° C. about 65° C. to about 75° C., or about 70° C. to about 80° C.

In some embodiments, the esterifying is catalyzed by Bi(OTf)$_3$, at a pressure of less than 5 torr or greater than 15 torr abs, and a temperature of about 50° C. to about 60° C. about 55° C. to about 65° C., about 60° C. to about 70° C. about 65° C. to about 75° C., or about 70° C. to about 80° C. In certain embodiments, estolide base oil is esterified with at least one alcohol in the presence of an esterification catalyst, optionally in the presence of applied microwave radiation.

In certain embodiments, a process for preparing an estolide base oil is provided that comprises providing at least one fatty acid reactant, at least one second fatty acid reactant and a Lewis acid catalysts, wherein the at least one first fatty acid reactant is an unsaturated fatty acid or an oligomer of unsaturated fatty acids and/or the at least one second fatty acid reactant is an unsaturated fatty acid or an oligomer of unsaturated fatty acids, and the Lewis acid catalyst is a triflate. In certain embodiments, the Lewis acid catalyst is selected from AgOTf, Cu(OTf)$_2$, Fe(OTf)$_2$, Fe(OTf)$_3$, NaOTf, LiOTf, Yb(OTf)$_3$, Y(OTf)$_3$, Zn(OTf)$_2$, Ni(OTf)$_2$, Bi(OTf)$_3$, La(OTf)$_3$, Sc(OTf)$_3$, and combinations thereof.

In certain embodiments, a process for preparing an estolide base oil is provided that comprises providing at least one fatty acid reactant, at least one second fatty acid reactant and a Lewis acid catalysts, wherein the at least one first fatty acid reactant is an unsaturated fatty acid or an oligomer of unsaturated fatty acids and/or the at least one second fatty acid reactant is an unsaturated fatty acid or an oligomer of unsaturated fatty acids, and the Lewis acid catalyst is an iron compound. In certain embodiments, the catalyst is a Lewis acid selected from Fe(acac)$_3$, FeCl$_3$, Fe$_2$(SO$_4$)$_3$, Fe$_2$O$_3$, FeSO$_4$, and combinations thereof. In certain embodiments, the process further includes use of a Bronsted acid as a catalyst wherein the Bronsted acid is sulfamic acid, methylsulfamic acid or combinations thereof.

In certain embodiments, the process for preparing an estolide base oil is a continuous process, wherein the catalyst is a Lewis acid selected from Fe(acac)$_3$, FeCl$_3$, Fe$_2$(SO$_4$)$_3$, Fe$_2$O$_3$, FeSO$_4$, and combinations thereof, and the process optionally further includes use of a Bronsted acid as a catalyst wherein the Bronsted acid is sulfamic acid, methylsulfamic acid or combinations thereof.

In certain embodiments estolide compounds and compositions are produced by a process comprising providing at least one first fatty acid reactant, at least one second fatty acid reactant, and a Lewis acid catalyst; and oligomerizing the at least one first fatty acid reactant with the at least one second fatty acid reactant in the presence of the Lewis acid catalyst to produce an estolide compound and/or estolide composition.

In certain embodiments, the at least one first fatty acid reactant is selected from one or more unsaturated fatty acids, one or more unsaturated fatty acid oligomers, and combinations thereof. In some embodiments, the at least one second fatty acid reactant is selected from saturated and unsaturated fatty acids, saturated and unsaturated fatty acid oligomers, and combinations thereof.

Without being bound to any particular theory, in certain embodiments, it is believed that an estolide is formed when a Lewis acid catalyst is used to produce a carbocation at a site of unsaturation on either a first or second fatty acid reactant, which is followed by nucleophilic attack on the carbocation by the carboxylic group of the other fatty acid. As noted above, in certain embodiments, suitable unsaturated fatty acids for preparing the estolides may include any mono- or polyunsaturated fatty acid. For example, in some embodiments, monounsaturated fatty acids, along with a suitable catalyst, will form a single carbocation for the addition of a second fatty acid (saturated or unsaturated), whereby a covalent bond between two fatty acid is formed. Suitable monounsaturated fatty acids may include, but are not limited to, palmitoleic (16:1), vaccenic (18:1), oleic acid (18:1), eicosenoic acid (20:1), erucic acid (22:1), and nervonic acid (24:1). In addition, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5).

In certain embodiments, the process for preparing the estolide compounds may include the use of any natural or synthetic fatty acid source. However, it may be desirable to source the fatty acids from a renewable biological feedstock.

In some embodiments, suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel based materials and other sources of the materials desired.

In certain embodiments, Lewis acid catalysts for preparing the estolides may include triflates (trifluormethanesulfonates) such as transition metal triflates and lanthanide triflates. Suitable triflates may include AgOTf (silver triflate), $Cu(OTf)_2$ (copper triflate), NaOTf (sodium triflate), $Fe(OTf)_2$ (iron (II) triflate), $Fe(OTf)_3$ (iron (III) triflate), LiOTf (lithium triflate), $Yb(OTf)_3$ (ytterbium triflate), $Y(OTf)_3$ (yttrium triflate), $Zn(OTf)_2$ (zinc triflate), $Ni(OTf)_2$ (nickel triflate), $Bi(OTf)_3$ (bismuth triflate), $La(OTf)_3$ (lanthanum triflate), $Sc(OTf)_3$ (scandium triflate), and combinations thereof. In some embodiments, the Lewis acid catalyst is $Fe(OTf)_3$. In some embodiments, the Lewis acid catalyst is $Bi(OTf)_3$.

In certain embodiments, Lewis acid catalysts may include metal compounds, such as iron compounds, cobalt compounds, nickel compounds, and combinations thereof. In some embodiments, the metal compounds may be selected from $FeX_n$ (n=2, 3), $Fe(CO)_5$, $Fe_3(CO)_{12}$, $Fe(CO)_3(ET)$, $Fe(CO)_3(DE)$, $Fe(DE)_2$, $CpFeX(CO)_2$, $[CpFe(CO)_2]_2$, $[Cp*Fe(CO)_2]_2$, $Fe(acac)_3$, $Fe(OAc)_n$ (n=2, 3), $CoX_2$, $CO_2(CO)_8$, $Co(acac)_n$, (n=2, 3), $Co(OAc)_2$, $CpCO(CO)_2$, $Cp*Co(CO)_2$, $NiX_2$, $Ni(CO)_4$, $Ni(DE)_2$, $Ni(acac)_2$, $Ni(OAc)_2$, and combinations thereof, wherein X is selected from hydrogen, halogen, hydroxyl, cyano, alkoxy, carboxylato, and thiocyanato; wherein Cp is a cyclopentadienyl group; acac is an acetylacetonato group; DE is selected from norbornadienyl, 1,5-cyclooctadienyl, and 1,5-hexadienyl; ET is selected from ethylenyl and cyclooctenyl; and OAc represents an acetate group. In some embodiments, the Lewis acid is an iron compound. In some embodiments, the Lewis acid is an iron compound selected from $Fe(acac)_3$, $FeCl_3$, $Fe_2(SO_4)_3$, $Fe_2O_3$, $FeSO_4$, and combinations thereof.

In some embodiments, the oligomerization process comprises use of one or more of protic or aprotic catalysts.

In some embodiments, the oligomerization processes are aided by the application of electromagnetic energy. In certain embodiments, the electromagnetic energy used to aid the oligomerization is microwave electromagnetic energy. In certain embodiments, for example, application of electromagnetic radiation may be applied to reduce the overall reaction time and improve the yield of estolide by conducting the reaction in a microwave reactor in the presence of an oligomerization catalyst. In some embodiments, oligomerizing the at least one first fatty acid reactant with the at least one second fatty acid reactant is conducted in the presence of an oligomerization catalyst (e.g., a Lewis acid) and microwave radiation. In some embodiments, the oligomerization is conducted in a microwave reactor with $Bi(OTf)_3$.

In some embodiments, the processes may further comprise the use of one or more Bronsted acids. For example, in some embodiments, the oligomerizing step may further comprise the presence of a Bronsted acid. Exemplary Bronsted acids include, but are not limited to, hydrochloric acid, nitric acid, sulfamic acid, methylsulfamic acid, sulfuric acid, phosphoric acid, perchloric acid, triflic acid, p-toluenesulfonic acid (p-TsOH), and combinations thereof. In some embodiments, the Bronsted acid is selected from sulfamic acid, methylsulfamic acid, and combinations thereof. In some embodiments, the Bronsted acid may comprise cation exchange resins, acid exchange resins and/or solid-supported acids. Such materials may include styrene-divinylbenzene copolymer-based strong cation exchange resins such as Amberlyst® (Rohm & Haas; Philadelphia, Pa.), Dowex® (Dow; Midland, Mich.), CG resins from Resintech, Inc. (West Berlin, N.J.), and Lewatit resins such as MonoPlus™ S 100H from Sybron Chemicals Inc. (Birmingham, N.J.). Exemplary solid acid catalysts include cation exchange resins, such as Amberlyst® 15, Amberlyst® 35, Amberlite® 120, Dowex® Monosphere M-31, Dowex® Monosphere DR-2030, and acidic and acid-activated mesoporous materials and natural clays such a kaolinites, bentonites, attapulgites, montmorillonites, and zeolites. Exemplary catalysts are also included organic acids supported on mesoporous materials derived from polysaccharides and activated carbon, such as Starbon®—supported sulphonic acid catalysts (University of York) like Starbon® 300, Starbon® 400, and Starbon® 800. Phosphoric acids on solid supports may also be suitable, such as phosphoric acid supported on silica (e.g., SPA-2 catalysts sold by Sigma-Aldrich).

In certain embodiments, fluorinated sulfonic acid polymers may be used as solid-acid catalysts for the processes described herein. These acids are partially or totally fluorinated hydrocarbon polymers containing pendant sulfonic acid groups, which may be partially or totally converted to the salt form. Exemplary sulfonic acid polymers include Nafion® perfluorinated sulfonic acid polymers such as Nation® SAC-13 (E.I. du Pont de Nemours and Company, Wilmington, Del.). In certain embodiments, the catalyst includes Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton ($H^+$), or the metal salt form.

In some embodiments, depending on the nature of the catalyst and the reaction conditions, it may be desirable to carry out the process at a certain temperature and/or pressure. In some embodiments, for example, suitable temperatures for effecting oligomerization may include temperatures greater than about 50° C., such as a range of about 50° C. to about 100° C. In some embodiments, the oligomerization is carried out at about 60° C. to about 80° C. In some embodiments, the oligomerization is carried out, for at least a portion of the time, at about 50° C., about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., and about 100° C. In some embodiments, the oligomerization is carried out, for at least a period of time, at a temperature of no greater than about 52° C., about 54° C., about 56° C., about 58° C., about 60° C., about 62° C., about 64° C., about 66° C., about 68° C., about 70° C., about 72° C., about 74° C., about 76° C., about 78° C., about 80° C., about 82° C., about 84° C., about 86° C., about 88° C., about 90° C., about 92° C., about 94° C., about 96° C., about 98° C., or about 100° C.

In some embodiments, suitable oligomerization conditions may include reactions that are carried out at a pressure of less than 1 atm abs (absolute), such at less than about 250 torr abs, less than about 100 torr abs, less than about 50 torr abs, or less than about 25 torr abs. In some embodiments, oligomerization is carried out at a pressure of about 1 torr abs to about 20 torr abs, or about 5 torr abs to about 15 torr abs. In some embodiments, oligomerization, for at least a period of time, is carried out at a pressure of greater than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, and about 250 torrs abs. In some embodiments, oligomerization, for at least a period of time, is carried out at a pressure of less than about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, or about 250 torrs abs. In some embodiments, the processes described herein further comprise the step of esterifying the resulting free acid estolide in the presence of at least one esterification catalyst. Suitable esterification catalysts may include one or more Lewis acids and/or Bronsted acids, including, for A example, AgOTf, $Cu(OTf)_2$, $Fe(OTf)_2$, $Fe(OTf)_3$, NaOTf, LiOTf, $Yb(OTf)_3$, $Y(OTf)_3$, $Zn(OTf)_2$, $Ni(OTf)_2$, $Bi(OTf)_3$, $La(OTf)_3$, $Sc(OTf)_3$, hydrochloric acid, nitric acid, sulfuric acid, phosphoric acid, perchloric acid, triflic acid, p-TsOH, and combinations thereof. In some embodiments, the esterification catalyst may comprise a strong Lewis acid such as $BF_3$ etherate. In some embodiments, the Lewis acid of the oligomerizing step and the esterification catalyst will be the same, such as $Bi(OTf)_3$. In some embodiments, the esterification is conducted in the presence of microwave radiation.

In some embodiments, the esterification catalyst may comprise a Lewis acid catalyst, example, at least one metal compound selected from titanium compounds, tin compounds, zirconium compounds, hafnium compounds, and combinations thereof. In some embodiments, the Lewis acid esterification catalyst is at least one titanium compound selected from $TiCl_4$, $Ti(OCH_2CH_2CH_2CH_3)_4$ (titanium (IV) butoxide), and combinations thereof. In some embodiments, the Lewis acid esterification catalyst is at least one tin compound selected from $Sn(O_2CCO_2)$ (tin (II) oxalate), SnO, $SnCl_2$, and combinations thereof. In some embodiments, the Lewis acid esterification catalyst is at least one zirconium compound selected from $ZrCl_4$, $ZrOCl_2$, $ZrO(NO_3)_2$, $ZrO(SO_4)$, $ZrO(CH_3COO)_2$, and combinations thereof. In some embodiments, the Lewis acid esterification catalyst is at least one hafnium compound selected from $HfCl_2$, $HfOCl_2$, and combinations thereof. Unless stated otherwise, all metal compounds and catalysts discussed herein should be understood to include their hydrate and solvate forms. For example, in some embodiments, the Lewis acid esterification catalyst may be selected from $ZrOCl_2.8H_2O$ and $ZrOCl_2.2THF$, or $HfOCl_2.2THF$ and $HfOCl_2-8H_2O$.

Also described herein is a process of producing a carboxylic acid ester, comprising:
providing at least one carboxylic acid reactant, at least one olefin, and a Bismuth catalyst; and
reacting the at least one carboxylic acid reactant with the at least one olefin in the presence of the Bismuth catalyst to produce a carboxylic acid ester.

In certain embodiments, the carboxylic acid reactant(s) may comprise an aliphatic carboxylic acid, such as an optionally substituted fatty acid that is branched or unbranched and saturated or unsaturated. It should be understood that aliphatic carboxylic acids may include cyclic and acyclic carboxylic acids. Other examples of aliphatic carboxylic acids may include acetic acid, propionic acid, butyric acid, isobutyric acid, acrylic acid, methacrylic acid, and the like.

In some embodiments, the carboxylic acid reactant may comprise any of the fatty acid reactants previously described herein, such as fatty acid oligomers and free fatty acid estolides. In some embodiments, the carboxylic acid reactant may comprise aromatic carboxylic acids such as benzoic acid, anisic acid, phenylacetic acid, salicylic acid, o-toluic acid, phthalic acid, isophthalic acid, terephthalic acid, and the like. In some embodiments, the at least one olefin may be optionally substituted and branched or unbranched. Suitable olefins may include aliphatic olefins and aromatic olefins. Aliphatic olefins include cyclic and acyclic olefins. In some embodiments, aliphatic olefins may include ethylene, propylene, isopropylene, butene, pentene, hexene, heptene, octane, and the like. Examples of the aromatic olefins include styrene, divinylbenzene, 1-vinylnaphthalene, 2-vinylnaphthalene, vinylpyridine, and the like.

Examples of cyclic olefins include a monocyclic olefin, and a bridged cyclic hydrocarbon represented by a bicyclo compound such as norbornenes which have distortion in the cyclic structure. Examples of the monocyclic olefin include a cyclic olefin with 3-6 carbon atoms such as cyclopropene, cyclobutene, cyclopentene, methylcyclopentene, and cyclohexene. Substituents for the carboxylic acid reactants and olefins may include any substituent that are appropriate as substituents for estolide compounds.

In some embodiments, the processes described herein may comprise a continuous flow process. The continuous flow processes may comprise the use of an oligomerization catalyst. In some embodiments, the continuous flow processes comprise use of a Lewis acid catalyst. In some embodiments a continuous process for producing an estolide base oil comprises: providing at least one first fatty acid reactant, at least one second fatty acid reactant, and an oligomerization catalyst; and continuously oligomerizing the at least one first fatty acid reactant with the at least one second fatty acid reactant in the presence of the oligomerization catalyst to produce an estolide base oil.

Unless otherwise stated, it should be understood that suitable materials, conditions, and compounds for practicing the continuous process may include the materials, conditions, and compounds, discussed herein for producing estolides, estolide base oils, and compositions comprising estolides.

In some embodiments, at least one first fatty acid reactant and at least one oligomerization catalyst are continuously provided to a region or location where the at least one fatty acid reactant reacts to form estolides and/or esters. In some embodiments, the at least one oligomerization catalyst catalyzes the oligomerization and/or esterification. In some embodiments, a first fatty acid reactant and at least one oligomerization catalyst are continuously provided at intervals, for example, at intervals of time including 1, 2, 3, 4, 5, 6, 7, 8, 9, 10, 15, 20, 25, 30, 35, 40, 50, and 60 minutes, and 2, 3, 4, 5, 6, or 7 hours, or, for example, intervals measured by degree of reaction completion including 5, 10, 15, 20, 25, 30, 35, 40, 45, 50, 55, 60, 65, 70, 75, 80, 85, 90, and 95% completion.

In some embodiments, at least one first fatty acid reactant and at least one second fatty acid reactant are continuously oligomerized in a reactor. In some embodiments, exemplary reactors include single vessels with a substantial degree of back-mixing, with or without mechanical agitation, such that the dwell time within the vessel of an identified portion of entering material is more or less random (e.g., "continuous stir tank reactor"). In some embodiments, reactors or reaction vessels may optionally include a heater or heat source. In some embodiments, the reactors or reaction vessels may include, upon operation, a quantity of liquid and a quantity of vapor. In some embodiments, the quantity of liquid will contain a greater fraction of estolide(s) relative to fatty acid reactant than the fraction of estolide(s) relative to fatty acid reactant in the quantity of vapor. In certain embodiments, a point of exit for vapor and/or a point of exit for liquid reactants and/or products will be provided.

In certain embodiments, reactor(s) may be a sequence(s) of back-mixed vessels, wherein the reaction mixture from one vessel constitutes the feed for a further vessel. In some embodiments, there is a combination of vessels and material is exchanged between them. In certain embodiments, the exchange of material between vessels in a combination is sufficiently rapid that a main flow of material into and/or out of the combination of vessels does not prevent the combination from acting as a single fully-back-mixed or partially-back-mixed vessel. Other embodiments may include horizontal or vertical vessels of large ratio of length to cross-sectional linear dimension (i.e., pipes and columns) through which the reacting material flows and in which identified portions of the material pass any point along the length in approximately the same order as at any other point (commonly known as "plug flow").

In certain embodiments, the temperature of the reactor(s) and/or reaction vessels may be controlled. In some embodiments, the temperature of the reactor(s) and/or reaction vessels can be controlled to provide zones or regions of differing temperature. In some embodiments, heat energy may be supplied along the length of the vessel(s) to conduct the oligomerization and/or to improve flow of material within the vessel(s) by decreasing the viscosity of reactants and/or products.

In certain embodiments, the reactor and/or reaction vessels may have the character that material introduced in the reactor and/or reaction vessels will pass from a first region where introduced in the reactor to increasing distal regions by flow and/or transport in a liquid and/or vapor state. In certain embodiments, the reactor and/or reaction vessel is a pipe or column optionally provided with one or more partial barriers which allow passage of fluid in the desired directions. In certain embodiments, the passage of fluid in directions other than the desired direction can be prevented or lessened by one or more partial barriers which allow passage of fluid in a desired direction, but which largely prevent back-flow of fluid.

In certain embodiments, combinations of back-mixed vessels and pipes or columns are used, optionally in sequence. In some embodiments, the reactor may comprise vessels incorporating large vertical surfaces, down which the reaction mixture flows and reacts. Vessels may, for example, in certain embodiments be designed to increase the available surface area relative to that available on flat or simple curved surfaces.

In certain embodiments, hybrid batch-continuous systems may be used, where at least a part of the process is carried out in each mode. In certain embodiments, the feed material is prepared in batches and fed continuously to a continuous reactor, and/or the product of the continuous reactor is further processed as individual batches.

In certain embodiments, the process is conducted in a semi-continuous reactor wherein both periodical and continuous charging of the reactor with reactants is combined with only periodic discharge of resulting product. For example, in certain embodiments of semi-continuous reactors, one or more initial reactants is charged in full, while a second or further reactant is only supplied gradually until the one or more initial reactants is exhausted. In other embodiments, semi-continuous reactors can comprise periodic discharge of the product or a mixture of product and reactants when a particular degree of completion has been attained. For example, in certain embodiments, the degree of completion for a semi-continuous reactor may be 10, 20, 30, 40, 50, 60, 70, 80, 90, or 100%.

In certain embodiments, a continuous process is carried out in a tank reactor such as a continuous stirred tank reactor. FIG. 1 illustrates exemplary process system 100, which includes continuous stirred tank reactor 102 and separation unit 104. Reactor 102 may be equipped with paddle stirrer 108 and, optionally, a heat source, which may or may not be located within the reaction medium. The heat source may be an internal replaceable heat source that comprises a non-fluid heating media. By replaceable, it is meant that the heat source can be replaced without the need to shut down the equipment to remove if a heater burns out. In some embodiments, for example, there can be an internal heater located centrally to the reactor. In certain embodiments, the heat source for reactor 102 may be in the form of an external jacket through which hot oil, warm water, or steam which may or may not be saturated, may be used to heat the reactor vessel.

In some embodiments, continuous processes may be performed by introducing one or more fatty acid reactants and an oligomerization catalyst into reactor 102 via inlet 106. Preparation of the desired estolide oligomer may be controlled by, for example, catalyst content, residence time of the reactants, stir rate, temperature, pressure, or a combination thereof. By continuously providing reactants and catalyst to reactor 102, it may be possible to control the size of the oligomer product recovered from the reactor(s). In some embodiments, for example, by continuously providing catalyst and reactants, and decreasing residence time, the oligomer products obtained will be smaller oligomers (e.g., estolides having a lower EN). Resulting oligomers can then be removed from reactor 102 via outlet 132. Opening valve 116 and closing valve 122 will allow for the transport of the oligomer product along conduit 110 to a secondary site for storage or, optionally, further processing (e.g., esterification, catalyst removal or recovery, or continued oligomerization). If desired, opening valve 114 and closing valve 116 will allow for the return of the oligomers and/or fatty acids to reactor 102 via conduit 112 for further oligomerization. Accordingly, in certain embodiments the continuous process comprises oligomerizing the reactants to form one or more first estolides. In some embodiments, at least a portion of the one or more first estolides is removed from the reactor. In certain embodiments, at least a portion of the one or more first estolides is transferred back to the reactor, or to a secondary reactor, for continued oligomerization to provide one or more second estolides. In some embodiments, the one or more second estolides have an EN that is greater than the EN of the one or more first estolides.

As noted above, in certain embodiments, the size of the estolides may be increased by increasing the residence time of the reactants in reactor 102, or by removing and subsequently returning a portion of the oligomers to the reactor for further processing. In certain embodiments, the desired EN for the oligomers is achieved, opening valve 122 and closing valve 116 allows for the transfer of the estolides to separation unit 104 via inlet 124. Separation unit 104 may be used to separate the estolides into two or more groups of varying size. Separation unit 104 may implement any suitable separation technique, including distillation, phase separation, chromatography, membrane separation, affinity separation, solvent extraction, or combinations thereof. As discussed further below with respect to FIG. 2, separation unit 104 may comprise a structure that is substantially similar to that of column reactor 200. Smaller oligomers (lower EN) may be transferred out of separation unit 104 via outlet 120, while larger oligomers (larger EN) can be removed via outlet 128. Thus, in some embodiments, the processes described herein comprise transferring estolides from the reactor to a separation unit for separation into one or more estolide products. In turn, in some embodiments, the one or more estolide products can be transferred from separation unit 104 to one or more secondary reactors for further processing (e.g., esterification, oligomerization) or may be transferred to storage.

Figure 2:
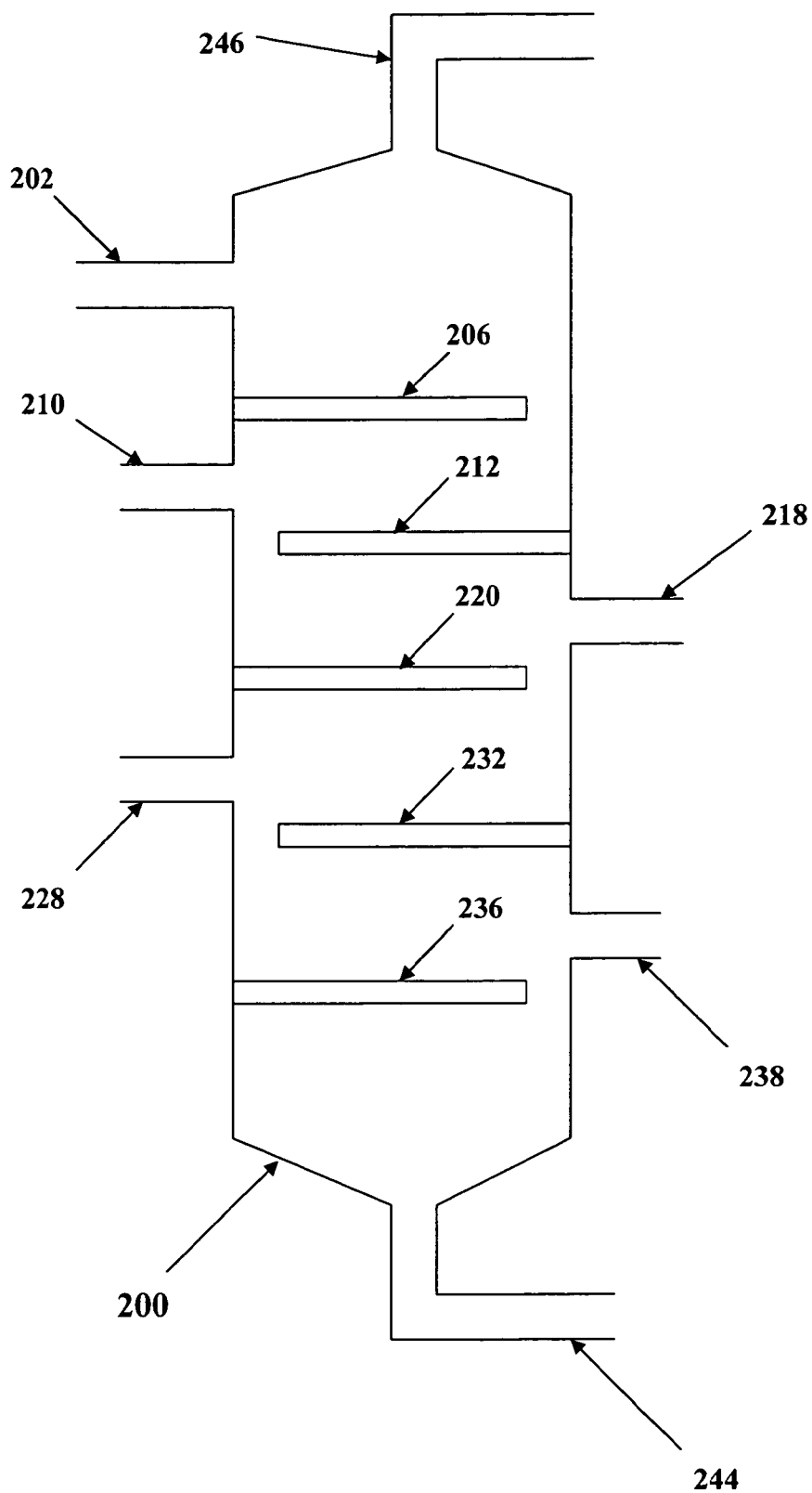
FIG. 2. schematically illustrates a column reactor useful for the processes for synthesis of estolides according to certain embodiments.

In certain embodiments, the reactor(s) or reaction vessels relate to column reactors. Exemplary reactors for the processes described herein may also include column reactors (e.g., vertical column reactors), and plug flow reactors. While a number of column reactor configurations are possible, vertical column reactor 200 is illustrated in FIG. 2. And while the term "vertical" suggests substantially vertical, it is understood that there can be tilt or angle to the reactor.

FIG. 2 illustrates a column reactor useful for the processes for synthesis of estolides according to certain embodiments. Column reactors can either be in a single stage or multiple stage configuration. In some embodiments, the column reactor has multiple stages, such as reactor 200, which has five stages (206, 212, 220, 232, and 236). If the reactor is co-current, the reaction mixture (reactants, oligomers, estolides) flow in one direction. In a counter-current reactor, the stages are designed to allow smaller materials (fatty acid reactants, smaller oligomers) to flow in a direction opposite to that of larger materials (larger oligomers/estolides). While the process of this reaction can be performed in a single stage reactor, processes comprise the use of at least two stages, and in some embodiments the process described herein comprise the use of at least 3, 4, 5, 6, 7, 8, 9, or 10 stages. In certain embodiments, the reactor has 5, 10, 15, 20, 25, 30, 35, 40, 45, 50, 60, 70, 80, or 100 stages.

In some embodiments, the results of the processes described herein may be improved by creating more efficient heat transfer from the column to the reactant(s). In certain embodiments, this may be accomplished by designing the column wall configuration or by placing good heat transfer materials such as glass beads of optimum surface to volume ratio in each stage of the column. Alternatively, in certain embodiments, it may be accomplished by providing a heat source located within the reaction medium.

In certain embodiments, depending on the manner in which reactor 200 is used, stages 206, 212, 220, 232, and 236 may represent either a packed bed or a fractioning tray. A stage that is in the form of a packed bed may or may not be composed of a catalyst. As noted above with respect to FIG. 1, in certain embodiments, separation unit 104 may comprise a structure that is substantially similar to that of reactor 200. In certain embodiments, a separation unit 104 comprising a structure that is substantially similar to that of reactor 200 may allow for more efficient separation of the estolides prepared in reactor 102. For example, in some embodiments, the stages may comprise a packed bed containing a structured or random packing of rings and saddles, or a combination of packed beds and fractioning trays. Thus, in certain embodiments, the process comprises the use of both a continuous stirred tank reactor and a separation column. In certain embodiments, use of a configuration with both a continuous stirred tank reactor and a separation column may be desirable in circumstances where the oligomerization catalyst is more easily handled in a tank reactor.

In certain embodiments, oligomerization may take place in the column reactor itself. In certain embodiments, catalyst will be fed into the reactor simultaneously with the fatty acid or oligomer feed stream. In certain embodiments, the one or more catalysts present in the reactor will be present in the form of one or more packed beds. In certain embodiments, one or more catalysts will be fed into a reactor before the fatty acid or oligomer feed enters the reactor. In certain embodiments, the one or more catalysts will be fed into a reactor after the fatty acid or oligomer feed enters the reactor. In certain embodiments, the fatty acid and/or oligomer feed streams may be introduced into a reactor and/or into reaction vessels at or near the top, at or near the bottom, or at any other stage within the reactor and/or reaction vessels. In certain embodiments, the one or more catalysts may be introduced into a reactor and/or into reaction vessels at or near the top, at or near the bottom, or at any other stage within the reactor and/or reaction vessels.

In certain embodiments, the process is a counter-current process as described with reference to FIG. 2. In certain embodiments, an oligomerization catalyst, such as a solid support catalyst, may be positioned in reaction stage 212, and optionally in one or more of stages 206, 220, 232, and 236. For example, in certain embodiments stage 212 may represent a packed bed structure with one or more theoretical trays that comprises the catalyst. One or more fatty acid reactants are then introduced to reaction stage 212 via conduit 210. As oligomerization proceeds in stage 212, the process stream of reactants and/or oligomerized products passes down through the stages. The stages are designed such that the reaction mixture flows downwardly while reactants and smaller oligomers are allowed to flow upwardly back to stage 212 or up to 206. While temperature may be uniform throughout the column, varying the temperature at different stages may allow the operator to control the oligomerization process and isolate estolides of a specific size at each stage. For example, by defining a temperature and pressure at stage 232, all reactants or oligomers that would be a vapor at that condition will vaporize and flow upward through stage 220 thereby leaving only compounds that are liquid at the defined conditions. Reactants and initial oligomerization products within the reactor may flow down into one or more stages, such as stages 220 and 232. By operating stages 220 and 232 at temperatures that are greater than stage 212, it may be possible to isolate estolide oligomers of a specific size, while forcing unreacted reactants and smaller oligomers back up into stage 212 for continued oligomerization. For example, in certain embodiments, a tray design for stages 220 and 232 allows for the collection of larger estolide products. Perforations in the tray design of barrier 220 (e.g., bubble cap design) would allow for the passage of reactants and smaller oligomers back up into stage 220 from stage 232 and, depending on the temperature of that stage, further passage into the packed bed of stage 212 for continued oligomerization. Thus, in some embodiments, the process described herein comprises oligomerizing at least one fatty acid reactant in a first reaction stage to provide an initial oligomerized product. In certain embodiments, at least a portion of the initial oligomerized product is transferred to at least one second reaction stage, wherein the initial oligomerized product is separated into one or more first estolides and one or more second estolides. In certain embodiments, the one or more second estolides will be larger than the one or more first estolides, wherein the one or more second estolides have an EN that is greater than the one or more first estolides. In certain embodiments, at least a portion of the one or more first estolides are returned to the first reaction stage for continued oligomerization.

By continuously providing reactor 200 with fatty acid reactants and catalyst (if catalyst is not already present within the reactor in the form of a packed bed), it is possible, in certain embodiments, to strictly control the size and rate at which the estolide oligomers are formed. In certain embodiments, the overall conversion to oligomers and extent of oligomerization within the reactor may be controlled by adjusting the number of actual or theoretical trays within the reactor, the temperature and pressure at each stage, the amount of catalyst either fed at each stage or already present in the reactor in the form of a packed bed, and/or the amount of reactants fed at each stage. In certain embodiments, as estolide sizes are increased, it may be possible to separate the products by controlling the temperature and/or pressure of each stage, as larger estolides typically exhibit higher boiling points. In certain embodiments, by controlling an increase in temperature at each successive stage (e.g., the temperature increases in going from 206 to 212, from 212 to 230, from 230 to 232, and from 232 to 236), larger estolide oligomers (higher EN) may be allowed to pass through further successive stages than smaller oligomers, which may be retained at certain stages and/or returned to earlier stages (e.g., stage 212). Thus, in certain embodiments, it may be possible to isolate estolides of specific sizes. In certain embodiments, the reactor may be designed to produce oligomers of a specific oligomer length which are collected at various stages. For example, stage 220 may be designed to collect medium size oligomers while stage 232 may be designed to collect larger size oligomers (higher EN). In certain embodiments, one or more conduits may be provided to transfer larger size oligomers from a reactor and/or reaction vessel. For example, a conduit tied into stage 232 may be used to transfer larger size oligomers from the reactor illustrated in FIG. 2. In certain embodiments, products and/or reactants transferred from a reactor and/or reaction vessel can be subjected to further processing or can be stored for a period of time.

In certain embodiments, the average estolide size can be increased by increasing the average EN of the estolide product. In some embodiments, the average EN at a given stage may be controlled by increasing the number of theoretical trays, including where the stage comprises or is in the form of a packed bed catalyst. In some embodiments, it may be possible to increase oligomer size in one or more of the subsequent stages by also providing oligomerization catalyst in one or more of stages 212, 220, 232, and 236. In certain embodiments, providing oligomerization catalyst in earlier stages may be accomplished by either adding more catalyst as a feed to one or more of these stages or by providing catalyst in a packed bed design for one or more stages. In certain embodiments, it may be possible to increase conversion of reactants to estolides and increase estolide size (higher EN) within the reactor or reaction vessels by including one or more pump-arounds where material within the reactor or reaction vessels is removed from one stage and pumped back up to a higher stage in the reactor and allowed to pass back through the stages (e.g., material removed via conduit 238 is reintroduced into the reactor via conduit 210).

In certain embodiments, the process may be operated at less than one atmosphere pressure. In some embodiments, application of sub-atmospheric pressure may facilitate removal of smaller oligomers and reactants from lower reaction stages, as well as the removal of any volatile impurities that may be present. Suitable temperatures and pressures may include those previously discussed herein.

In certain embodiments, the conversion from reactants to oligomers may take place in a "plug flow" reactor. In some embodiments, a plug flow reactor may be packed with one or more catalyst or the one or more catalyst may enter the reactor with reactants introduced into the reactor. In certain embodiments, the feed to the reactor may be continuous. In certain embodiments, conversion of reactants to oligomer product depends on residence time within the reactor. In certain embodiments, residence time within the reactor is a function of reactor length. In certain embodiments, therefore, the extent of oligomerization and/or EN of products can be affected by selection of the one or more catalyst, the amount of catalyst (catalyst loading), the volumetric flow rate of the feed, the length of the reactor, the pressure, the temperature(s) within the reactor, or combinations thereof.

In certain embodiments, suitable oligomerization catalysts may include Lewis acids, Bronsted acids, or combinations thereof, such as those previously described herein. In certain embodiments, certain catalysts, such as Lewis acids and/or solid-supported Bronsted acids, may be desirable for the continuous processes described herein. In certain embodiments, catalysts such as $Fe(OTf)_3$ and $Bi(OTf)_3$ may be recovered and reused, including, for example, in subsequent oligomerization processes. In certain embodiments, montmorillonite and/or zeolite catalysts may be recovered for reuse. In certain embodiments, oligomerization catalysts such as Amberlyst and Dowex may used by positioning the solid support in one or more stages of a reactor and/or reaction vessel.

The present disclosure further relates to methods of making estolides according to Formula I, II, and III. By way of example, the reaction of an unsaturated fatty acid with an organic acid and the esterification of the resulting free acid estolide are illustrated and discussed in the following Schemes I and II. The present disclosure further relates to catalysts used in methods of making estolides according to Formula I, II, and TR. The particular structural formulas used to illustrate the reactions correspond to those for synthesis of compounds according to Formula I and III; however, the methods apply equally to the synthesis of compounds according to Formula II, with use of compounds having structure corresponding to $R_3$ and $R_4$ with a reactive site of unsaturation.

As illustrated below, compound 100 represents an unsaturated fatty acid that may serve as the basis for preparing the estolide compounds and compositions comprising estolide compounds.

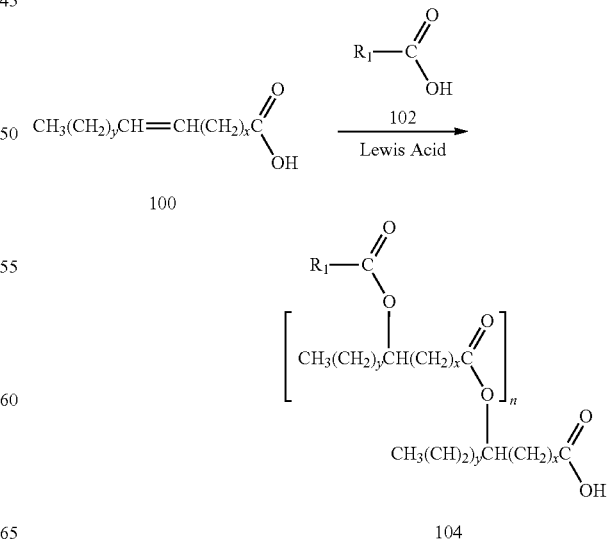

In Scheme 1, wherein x is, independently for each occurrence, an integer selected from 0 to 20, y is, independently for each occurrence, an integer selected from 0 to 20, and n is an integer greater than or equal to 1, unsaturated fatty acid 100 may be combined with compound 102 and a Lewis acid to form free acid estolide 104. In certain embodiments, it is not necessary to include compound 102, as unsaturated fatty acid 100 may be exposed alone to Lewis acid conditions to form free acid estolide 104, wherein $R_1$ would represent an unsaturated alkyl group. If compound 102 is included in the reaction, $R_1$ may represent one or more optionally substituted alkyl residues that are saturated or unsaturated and branched or unbranched. In certain embodiments, any suitable Lewis acid may be implemented to catalyze the formation of free acid estolide 104, including but not limited to triflates, iron compounds, cobalt compounds, nickel compounds, or combinations thereof. In certain embodiments, other catalysts may be used to catalyze the formation of free acid estolide 102. In certain embodiments, Bronsted acids, in addition to the Lewis acid, or in the alternative to the Lewis acid may be a catalyst. In some embodiments, Bronsted acid catalysts include homogenous acids and/or strong acids like hydrochloric acid, sulfuric acid, perchloric acid, nitric acid, triflic acid, and the like may be used in estolide synthesis. In some embodiments, solid-supported acid catalysts such as Amberlyst®, Dowex®, and Nafion® may also be used.

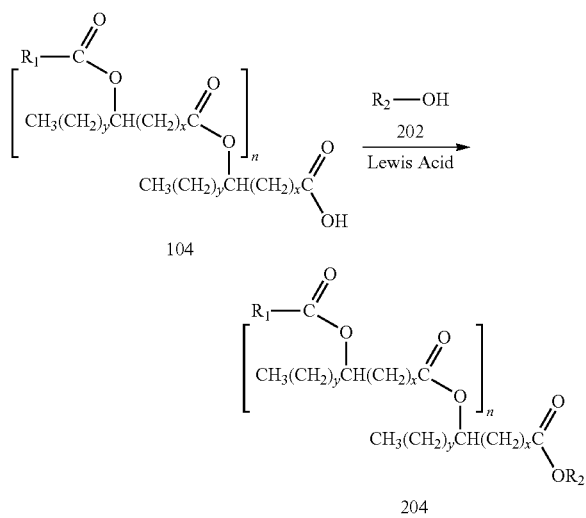

Scheme 2

Similarly, in Scheme 2, wherein x is, independently for each occurrence, an integer selected from 0 to 20, y is, independently for each occurrence, an integer selected from 0 to 20, and n is an integer greater than or equal to 1, free acid estolide 104 may be esterified by any suitable procedure known to those of skilled in the art, such as Lewis acid-catalyzed reduction with alcohol 202, to yield esterified estolide 204. Exemplary methods may include the use of strong Lewis acid catalysts such as $BF_3$. Other methods may include the use of triflates, titanium compounds, tin compounds, zirconium compounds, hafnium compounds, or combinations thereof.

As discussed above, in certain embodiments, the estolides described herein may have improved properties which render them useful as base stocks for biodegradable lubricant applications. Such applications may include, without limitation, crankcase oils, gearbox oils, hydraulic fluids, drilling fluids, dielectric fluids, greases two-cycle engine oils, greases, dielectric fluids, and the like. Other suitable uses may include marine applications, where biodegradability and toxicity are of concern. In certain embodiments, the nontoxic nature certain estolides described herein may also make them suitable for use as lubricants in the cosmetic and food industries.

In certain embodiments, estolide compounds may meet or exceed one or more of the specifications for certain end-use applications, without the need for conventional additives. For example, in certain instances, high-viscosity lubricants, such as those exhibiting a kinematic viscosity of greater than about 120 cSt at 40° C., or even greater than about 200 cSt at 40° C., may be desirable for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising an estolide base stock. For example, in certain embodiments, the estolides described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the estolides described herein may be co-blended with one or more synthetic or petroleum-based oils to achieve the desired viscosity and/or pour point profiles. In certain embodiments, certain estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:

NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1$H NMR by a peak at about 4.84 ppm.

Estolide Number (EN):

The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):

The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, and III, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:

The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):

GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:

To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M H$_2$SO$_4$/MeOH and heated at 100° C. for 15 minutes and then allowed to cool to room temperature. One (1) mL of H$_2$O and 1 mL of hexane were then added to the vial and the resulting liquid phases were mixed thoroughly. The layers were then allowed to phase separate for 1 minute. The bottom H$_2$O layer was removed and discarded. A small amount of drying agent (Na$_2$SO$_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \Sigma 100 \times \frac{A_f \times MW_I \times db}{MW_f}$$

$A_f$=fraction of fatty compound in the sample
$MW_I$=253.81, atomic weight of two iodine atoms added to a double bond
db=number of double bonds on the fatty compound
$MW_f$=molecular weight of the fatty compound Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapprovd 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

HPLC Analysis of Estolide Products:

To analyze the % formation of estolides from the processes described herein, HPLC may be used to determine the AUC (area under curve) for the estolide products.

Equipment:

HPLC with a Thermo Separations Spectra System AS 1000 autosampler/injector (Fremont, Calif.) and a P2000 binary gradient pump from Thermo Separation Products (Fremont, Calif.) coupled with an Alltech 500 ELSD evaporative light scattering detector (Alltech Associates, Deerfield, Ill.). Reverse-phase analysis performed using a Dynamax C-8 column (25 cm×4.6 mm i.d., 8 μm particle size, 60 Å pore size) from Agilent (Harbor City, Calif., part # r00083301c).

Parameters for Analysis:

Run time: 16 minutes. Mobile phase: gradient elution at a flow rate of 1 mL/min; 0-4 minutes, 80% acetonitrile, 20% acetone; 6-10 minutes, 100% acetone; 11-16 minutes, 80% acetonitrile, 20% acetone. The ELSD drift tube is set to 50° C. with the nebulizer set at 30 psi N$_2$, providing a flow rate of 2.0 standard liters per minute (SLPM). Full loop injection: 20 μL.

Sample Preparation:

Take a few drops of estolide sample and mix it with about 2-3 mL of hexane along with some pH 5 buffer (sodium phosphate, 500 g per 4 L) and thoroughly mix it. Remove the pH 5 buffer. Dry the sample with sodium sulfate. Take a few drops of the dried sample (amount depends on response of detector) and add it to a vial along with 1.75 mL of hexane. Sample is then ready for HPLC analysis.

Analysis:

Elution times: Estolides, 10.3 to 13.9 min; Oleic Acid, 5.5 min. $^1$H NMR is used to verify the presence of estolide by a peak at 4.84 ppm.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (µ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1µ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides.

Example 2

Bronsted and Lewis acid catalysts were tested for their ability to oligomerize fatty acid reactants into estolide products. In a glass vessel, oleic acid (1.0 equiv, 2.0 g, OL 700, Twin Rivers) was added with the catalyst under continuous stirring. The crude reaction product was then filtered and subjected to NMR analysis to confirm the formation of the estolide product. HPLC analysis was then used to determine the overall yield of the estolide product. Results for each of the catalysts are provided in Table 1 below:

TABLE 1

| Catalyst | Loading/Equiv. | Temp (° C.) | Time (hrs) | Yield (%) |
| --- | --- | --- | --- | --- |
| Amberlyst BD20 | 45 wt. % | 140 | 18 | 20.3 |
| Amberlyst 15 | 45 wt. % | 80 | 18 | 45.2 |
| Amberlyst 35 | 45 wt. % | 80 | 18 | 37.6 |
| Fe(OTf)$_3$ | 0.05 eq. | 60 | 18 | 56.1 |
| Bi(OTf)$_3$ | 0.05 eq. | 60 | 18 | 56.0 |
| Dowex Monosphere DR-2030 | 5 wt. % | 110 | 12 | 17.2 |
| Nafion SAC-13 | 45 wt. % | 110 | 16 | 16.4 |
| AgOTf | 0.05 eq. | 110 | 16 | 18.2 |
| Montmorillonite K10 | 30% | 110 | 14-18 | 22.8 |
| Zn(OTf)$_2$ | 0.05 eq. | 140 | 18 | 16.0 |
| Fe$_2$O$_3$ TfOH | 0.05 eq. 0.15 eq. | 60 | 18 | 53.8 |
| Fe$_2$(SO$_4$)$_3$ | 0.05 eq. | 110 | 18 | 9.5 |
| Fe$_2$(SO$_4$)$_3$ TfOH | 0.05 eq. 0.15 eq. | 60 | 18 | 49.8 |
| FeCl$_3$ TfOH | 0.05 eq. 0.15 eq. | 60 | 18 | 48.8 |
| FePO$_4$•xH$_2$O TfOH | 0.05 eq. 0.15 eq. | 110 | 18 | 19.3 |
| FeCl$_3$ AgOTf | 0.05 eq. 0.15 eq. | 80 | 18 | 47.3 |
| Cu(OTf)$_2$ | 0.05 eq. | 60 | 12 | 31.1 |
| FeSO$_4$ Ammonium persulfate | 0.05 eq. 0.50 eq. | 140 | 12 | 9.3 |

Example 3

The ability to recover catalyst from catalytic reaction(s) set forth in Example 2 was tested. After the reaction was complete, the crude, unfiltered reaction mixture was cooled and subjected to workup conditions that allowed for recovery and reuse of the catalyst. Results are set forth in Table 2.

TABLE 2

| Catalyst | Conditions | % Recovery |
| --- | --- | --- |
| Fe(OTf)$_3$ | Cooled reaction mixture was washed 3X with cold water. Combined aqueous phase was heated and dried under vacuum. | >90% |
| Bi(OTf)$_3$ | Hexanes are added to the cooled reaction mixture to precipitate the catalyst, which is filtered and isolated. | — |

Example 4

Catalysts recovered in Example 3 are recycled and tested for their ability to again convert fatty acid reactants into estolide products. Reaction conditions are substantially similar to those set forth in Example 2. The crude reaction products are then filtered and subjected to NMR analysis to confirm the formation of the estolide product. HPLC analysis is then used to determine the overall yield of the estolide product.

Example 5

Lewis acid catalysts were tested for their ability to esterify the free acid estolide product of Example 1 with 2-ethylhexanol (2-EH). In a glass vessel under N$_2$ equipped with condenser, water separator, and stir bar, the estolide product of Example 1 (1.0 equiv.) was added with 2-EH (4.0 equiv.) and the catalyst under continuous stirring. The reaction mixture was heated under continuous stirring, and water is removed from the water separator as needed. The crude reaction product was then distilled under vacuum at 100° C. to remove any unreacted alcohol. The reaction product was then filtered and subjected to NMR analysis to confirm the formation of the estolide product. HPLC analysis is used to determine that overall yield of the esterified product. Reaction conditions for each catalyst is are provided in Table 3 below:

TABLE 3

| Catalyst | Loading/Equiv. | Temp (° C.) | Time (hrs) |
| --- | --- | --- | --- |
| Amberlyst 15 | 6.7 wt. % | 120 | 3 |
| Amberlyst 35 | 6.7 wt. % | 120 | 3 |

TABLE 3-continued

| Catalyst | Loading/Equiv. | Temp (° C.) | Time (hrs) |
|---|---|---|---|
| Fe(OTf)$_3$ | 0.05 eq. | 120 | 3 |
| Bi(OTf)$_3$ | 0.05 eq. | 120 | 3 |
| Dowex Monosphere DR-2030 | 6.7 wt. % | 120 | 3 |
| Dowex 50WX8 (mesh 50-100) | 6.7 wt. % | 120 | 3 |
| Dowex 50WX8 (mesh 200-400) | 6.7 wt. % | 120 | 3 |
| Nafion SAC-13 | 6.7 wt. % | 120 | 3 |
| Nafion NR40 | 6.7 wt. % | 120 | 3 |
| AgOTf | 0.05 eq. | 120 | 3 |
| Montmorillonite K10 | 6.7 wt. % | 120 | 17 |
| Zn(OTf)$_2$ | 0.05 eq. | 120 | 3 |
| Zeolite (75% ZSM-5/25% Al$_2$O$_3$), Non-calcinated | 6.7 wt. % | 120 | 16 |
| Zeolite (75% ZSM-5/25% Al$_2$O$_3$), Calcinated | 6.7 wt. % | 120 | 16 |
| Zeolite ZSM-5, 18.2% P$_2$O$_5$ | 6.7 wt. % | 120 | 3 |
| NexCat (ZnO—La$_2$O$_3$) | 6.7 wt. % | 120 | 16 |
| Starbon 300 | 6.7 wt. % | 120 | 3 |
| Methylsulfamic acid | 0.05 eq. | 120 | 3 |
| Perchloric acid | 0.05 eq. | 120 | 3 |
| Phosphoric acid | 0.05 eq. | 120 | 3 |
| Cu(OTf)$_2$ | 0.05 eq. | 120 | 3 |
| SPA-2 | 6.7 wt. % | 120 | 3 |
| Ti(OCH$_2$CH$_2$CH$_2$CH$_3$)$_4$ | 0.03 eq. | 80 | 16 |
| | | 120 | 16 |
| | | 140 | 16 |
| | | 120 | 17 |
| | | 120 | 6 |
| | | 140 | 6 |
| Sn(O$_2$CCO$_2$) | 0.03 eq. | 80 | 16 |
| | | 120 | 16 |
| | | 140 | 16 |
| | | 120 | 17 |
| | | 120 | 6 |
| | | 140 | 6 |
| ZrOCl$_2$•8H$_2$O | 0.03 eq. | 80 | 16 |
| | | 120 | 16 |
| | | 140 | 16 |
| | | 120 | 6 |
| | | 140 | 6 |
| Potassium Bisulfate | 0.07 eq. | 120 | 17 |

Example 6

Catalyst recovery for the Sn(O$_2$CCO$_2$) reactions set forth in Example 5 is tested. Upon removal of the excess alcohol, the Sn(O$_2$CCO$_2$) precipitates from solution. The precipitated catalysts is then filtered and dried. The activity of the recovered catalyst is then tested by subjecting it to a synthetic procedure substantially similar to that set forth in Example 5.

Example 7

In a Biotage Initiator microwave reactor (100 watts) was placed a microwave reaction vial equipped with a magnetic stir bar, and oleic acid (1.0 equiv, OL 700, Twin Rivers) was added with the desired Lewis acid catalyst. Under continuous stirring, the reaction mixture was heated for 20 min in the microwave reactor. The crude reaction mixture was then cooled and filtered. HPLC analysis was then used to determine that overall yield of the estolide product. Results for each of the catalysts are provided below in Table 4:

TABLE 4

| Catalyst | Loading/Equiv. | Temp (° C.) | Yield (%) |
|---|---|---|---|
| Fe(OTf)$_3$ | 0.05 equiv. | 40 | 13.0 |
| | | 60 | 41.1 |
| | | 80 | 39.2 |
| | | 100 | 31.0 |
| Bi(OTf)$_3$ | 0.05 equiv. | 40 | 2.8 |
| | | 60 | 33.6 |
| | | 80 | 49.4 |
| | | 100 | 27.7 |

Example 8

In a Biotage Initiator microwave reactor (100 watts) was placed a microwave reaction vial equipped with a magnetic stir bar and the estolide product of Example 1 (1.0 equiv), Bi(OTf)$_3$ (0.1 equiv), and 2-EH (10 equiv). With continuous stirring, the reaction mixture was heated to 150° C. for 20 min in the microwave reactor. The crude reaction mixture was then cooled and filtered. HPLC analysis of the reaction mixture indicated a >90% yield of the esterified estolide.

Example 9

Estolides will be prepared according to the method set forth in Examples 1 and 5, except the 2-ethylhexanol esterifying alcohol is replaced with various other alcohols, including those identified below in Table 7:

TABLE 7

| Alcohol | Structure |
|---|---|
| Jarcol™ I-18CG | iso-octadecanol |
| Jarcol™ I-12 | 2-butyloctanol |
| Jarcol™ I-20 | 2-octyldodecanol |
| Jarcol™ I-16 | 2-hexyldecanol |
| Jarcol™ 85BJ | cis-9-octadecen-1-ol |
| Fineoxocol® 180 | (branched structure shown) |
| Jarcol™ I-18T | 2-octyldecanol |

Example 10

Estolides to be prepared according to the method set forth in Examples 1 and 5, except the 2-ethylhexanol esterifying alcohol will be replaced with various alcohols, including those set forth below in Table 8, which may be saturated or unsaturated and unbranched or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched or unbranched residue at the R$_2$ position:

TABLE 8

| Alcohol | R$_2$ Substituents |
|---|---|
| C$_1$ alkanol | methyl |
| C$_2$ alkanol | ethyl |

TABLE 8-continued

| Alcohol | R$_2$ Substituents |
|---|---|
| C$_3$ alkanol | n-propyl, isopropyl |
| C$_4$ alkanol | n-butyl, isobutyl, sec-butyl |
| C$_5$ alkanol | n-pentyl, isopentyl neopentyl |
| C$_6$ alkanol | n-hexyl, 2-methyl pentyl, 3-methyl pentyl, 2,2-dimethyl butyl, 2,3-dimethyl butyl |
| C$_7$ alkanol | n-heptyl and other structural isomers |
| C$_8$ alkanol | n-octyl and other structural isomers |
| C$_9$ alkanol | n-nonyl and other structural isomers |
| C$_{10}$ alkanol | n-decanyl and other structural isomers |
| C$_{11}$ alkanol | n-undecanyl and other structural isomers |
| C$_{12}$ alkanol | n-dodecanyl and other structural isomers |
| C$_{13}$ alkanol | n-tridecanyl and other structural isomers |
| C$_{14}$ alkanol | n-tetradecanyl and other structural isomers |
| C$_{15}$ alkanol | n-pentadecanyl and other structural isomers |
| C$_{16}$ alkanol | n-hexadecanyl and other structural isomers |
| C$_{17}$ alkanol | n-heptadecanyl and other structural isomers |
| C$_{18}$ alkanol | n-octadecanyl and other structural isomers |
| C$_{19}$ alkanol | n-nonadecanyl and other structural isomers |
| C$_{20}$ alkanol | n-icosanyl and other structural isomers |
| C$_{21}$ alkanol | n-heneicosanyl and other structural isomers |
| C$_{22}$ alkanol | n-docosanyl and other structural isomers |

Example 11

"Ready" and "ultimate" biodegradability of the estolide produced in Ex. 1 was tested according to standard OECD procedures. Results of the OECD biodegradability studies are set forth below in Table 9:

TABLE 9

| | 301D 28-Day (% degraded) | 302D Assay (% degraded) |
|---|---|---|
| Canola Oil | 86.9 | 78.9 |
| Ex. 1 Base Stock | 64 | 70.9 |

Example 12

The Ex. 1 estolide base stock was tested under OECD 203 for Acute Aquatic Toxicity. The tests showed that the estolides are nontoxic, as no deaths were reported for concentration ranges of 5,000 mg/L and 50,000 mg/L.

The invention claimed is:

1. A continuous process comprising:
continuously providing at least one first fatty acid reactant and at least one second fatty acid reactant; and
continuously oligomerizing the at least one first fatty acid reactant with the at least one second fatty acid reactant in the presence of a polymer-supported acid catalyst, to produce an estolide base oil.

2. The process according to claim 1, wherein the at least one first fatty acid reactant and the at least one second fatty acid reactant are continuously oligomerized in a reactor.

3. The process according to claim 2, wherein the reactor is equipped with a heat source.

4. The process according to claim 2, wherein the reactor is a microwave reactor.

5. The process according to claim 2, wherein the reactor is a continuous stirred tank reactor.

6. The process according to claim 1, wherein the oligomerizing produces one or more first estolides.

7. The process according to claim 2, wherein the reactor is a column reactor.

8. The process according to claim 7, wherein the reactor comprises a first reaction stage.

9. The process according to claim 8, wherein the reactor comprises two or more reaction stages.

10. The process according to claim 9, wherein the polymer-supported acid catalyst is present in one or more of the reaction stages.

11. The process according to claim 10, wherein the polymer-supported acid catalyst comprises a Bronsted acid.

12. The process according to claim 3, wherein the oligomerizing is carried out at a temperature that is greater than 50° C.

13. The process according to claim 12, wherein the oligomerizing is carried out at a temperature range of 50° C. to 100° C.

14. The process according to claim 2, wherein the reactor is a plug flow reactor.

15. The process according to claim 1, wherein the polymer-supported acid catalyst comprises a sulfonic acid polymer.

16. The process according to claim 15, wherein the polymer-supported acid catalyst comprises a fluorinated sulfonic acid polymer.

17. The process according to claim 1, further comprising esterifying the estolide base oil to provide an esterified estolide base oil.

18. The process according to claim 17, wherein the esterifying is conducted in the presence of an esterifying alcohol.

19. The process according to claim 17, further comprising hydrogenating the esterified estolide base oil.

* * * * *